(12) United States Patent
Ullah et al.

(10) Patent No.: US 10,533,079 B2
(45) Date of Patent: Jan. 14, 2020

(54) COPOLYMERS FOR IODIDE DETECTION AND METHODS THEREOF

(71) Applicant: King Fahd University of Petroleum and Minerals, Dhahran (SA)

(72) Inventors: Nisar Ullah, Dhahran (SA); Muhamad Mansha, Dhahran (SA); Manzar Sohail, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 16/006,217

(22) Filed: Jun. 12, 2018

(65) Prior Publication Data

US 2019/0248972 A1     Aug. 15, 2019

Related U.S. Application Data

(60) Provisional application No. 62/630,060, filed on Feb. 13, 2018.

(51) Int. Cl.
    *C08J 5/22*      (2006.01)
    *C08L 41/00*      (2006.01)
    *C07D 471/00*      (2006.01)

(52) U.S. Cl.
CPC .......... *C08J 5/2231* (2013.01); *C07D 471/00* (2013.01); *C08L 41/00* (2013.01); *C08J 2323/06* (2013.01); *C08J 2325/06* (2013.01); *C08J 2327/06* (2013.01); *C08J 2341/00* (2013.01); *C08L 2203/16* (2013.01)

(58) Field of Classification Search
CPC .. C08J 5/2231; C08J 2341/00; C08J 2325/06; C08J 2323/06; C08J 2327/06; C08L 41/00; C08L 2203/16
See application file for complete search history.

(56) References Cited

FOREIGN PATENT DOCUMENTS

| | | |
|---|---|---|
| KR | 2014-0025621 | 3/2014 |
| KR | 2014-0062610 | 5/2014 |
| WO | 2007/110062 A1 | 10/2007 |
| WO | 2014/077590 | 5/2014 |

OTHER PUBLICATIONS

Mi, Sai, et al.; Active and Electrochromic Bifunctional Polymer and a Device Composed thereof Synchronously Achieve Electrochemical Fluorescence Switching and Electrochromic Switching; ACS Applied Materials and Interfaces, 2015, 7 (49), pp. 27511-27517; Nov. 19, 2015; Abstract.

Biank, H. C., et al.; Optical spectroscopy of photovoltaic systems based on low-bandgap polymers; ScienceDirect, Thin Solid Films, vol. 560, pp. 77-81; Jun. 2, 2014; Abstract.

Sensfuss, S., et al.; Thienopyrazine-based low-bandgap polymers for flexible polymer solar cells; Eur. Phys. J. Appl. Phys. vol. 51, No. 3; Sep. 2, 2010; Abstract.

Liedtke, Alicia, et al.; White-Light OLEDs Using Liquid Crystal Polymer Networks; Chemistry of Materials, 2008, 20 (11), pp. 3579-3586; May 8, 2008; Abstract.

(Continued)

*Primary Examiner* — Shane Fang
(74) *Attorney, Agent, or Firm* — Oblon, McClelland, Maier & Neustadt, L.L.P.

(57) ABSTRACT

Copolymers having thiophene based and vinylene based moieties. Methods of producing the copolymers, and methods of utilizing the copolymers as chromogenic sensors for selective detection of iodide anion are also provided.

20 Claims, 21 Drawing Sheets

(56) References Cited

OTHER PUBLICATIONS

Shahid, Munazza, et al. ; Synthesis and Properties of Novel Low-Band-Gap Thienopyrazine-Based Poly(heteroartlenevinylene)s ; Macromolecules, 2006 , 39(23), pp. 7844-7853 ; Oct. 18, 2006 ; Abstract.
Mikroyannidis, John A., et al. ; Poly(fluorenevinylene) derivatives by Heck coupling: Synthesis, photophysics, and electroluminescence ; Journal of Polymer Science Part A: Polymer Chemistry / vol. 44, Issue 15 ; Jun. 20, 2006 ; Abstract.
Wu, Sheng-Han, et al. ; Synthesis and characterization of new light □ emitting copolymers in polymeric□ light□ emitting□ diode device fabrications ; Journal of Polymer Science Part A: Polymer Chemistry / vol. 42, Issue 16 ; Jul. 12, 2004 ; Abstract.
Mikroyannidis, John A., et al. ; Synthesis and optical properties of poly(p-phenylenevinylene)s bearing tetraphenylthiophene or dibenzothiophene moieties along the main chain ; ScienceDirect, Synthetic Metals, vol. 142, Issues 1-3, pp. 113-120 ; Apr. 13, 2004 ; Abstract.
Mehmood, Umer, et al. ; 3-Hexyl-2,5-diphenylthiophene:phenylene vinylene-based conjugated polymer for solar cells application ; ScienceDirect, Dyes and Pigaments, Column 144, pp. 218-222 ; Sep. 2017 ; Abstract.
Mansha, Muhammad, et al. ; Synthesis, characterization, and properties of new 3□ hexyl□ 2,5□ diphenylthiophene: Phenylene vinylenes copolymers as colorimetric sensor for iodide anion ; Journal of Applied Polymer Science, vol. 134, Issue 24 ; Feb. 13, 2017 ; Abstract.
Wu, Sheng-Han, et al. "Synthesis and luminescent properties of aromatic-thiophene copolymers" American Chemical Society, PMSE Preprints (2005), 92, 3-4 (Abstract Only).

COPOLYMERS FOR IODIDE DETECTION AND METHODS THEREOF

STATEMENT OF FUNDING ACKNOWLEDGEMENT

This project was funded by National Plan for Science, Technology, and Innovation (NSTIP) through project number 15-BIO3920-04 and King Fahd University of Petroleum and Minerals (KFUPM).

CROSS-REFERENCE TO RELATED APPLICATIONS

The present application claims priority to U.S. Provisional Application No. 62/630,060, filed Feb. 13, 2018, which is hereby incorporated by reference in its entirety for all purposes.

STATEMENT REGARDING PRIOR DISCLOSURE BY THE INVENTORS

Aspects of this technology are described in an article "Synthesis, characterization, and properties of new 3-hexyl-2,5-diphenylthiophene: Phenylene vinylenes copolymers as colorimetric sensor for iodide anion" published in Journal of Applied Polymer Science, 2017, 134, 44948, on Feb. 13, 2017, which is incorporated herein by reference in its entirety.

BACKGROUND OF THE INVENTION

Technical Field

The present disclosure relates to a copolymer and methods for its synthesis. Additionally, the present disclosure relates to applications of the copolymer as a chromogenic probe for chemical detection of iodide anions.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Conjugated polymers (CPs) have been widely used for the development of photovoltaic devices (PVDs) [Liu, C.; Yi, C.; Wang, K.; Yang, Y.; Bhatta, R. S.; Tsige, M.; Xiao, S; Gong, X. *ACS Appl. Mater. Interfaces* 2015, 7, 4928, and Heeger, A. *J. Chem. Soc. Rev.* 2010, 39, 2354], light emitting diodes (LEDs) [Grimsdale, A. C.; Chan, K. L.; Martin, R. E.; Jokisz, P. G.; Holmes, A. B. *Chem. Rev.* 2009, 109, 897], electrochromic devices (ECDs) [Mortimer, R. J.; Dyer, A. L.; Reynolds, J. R. *Displays* 2006, 27, 2] and field effect transistors (FETs) [Sonmez, G. *Chem. Commun.* 2005, 5251]. In particular, many of the parameters of interest are dependent on a CP's band gap (Eg), which is the energy between the filled valence and empty conduction bands and thus corresponds to the HOMO-LUMO gap (band edge) in the solid state. A donor-acceptor approach ("D-A") that constructs alternating electron rich (D) and electron poor (A) segments along a polymeric backbone is an effective way to produce CPs with narrow band gaps and desirable optoelectronic properties [Thomas, C. A.; Zong, K.; Abboud, K. A.; Steel, P. J.; Reynolds, J. R. *J. Am. Chem. Soc.* 2004, 126, 16440; Wienk, M. M.; Struijk, M. P.; Janssen, R. A. *J. Chem. Phys. Lett.* 2006, 422, 488; and Yang, Y. L.; Lee, Y. H.; Chang, C. J.; Lu, A. J.; Hsu, W. C.; Wang, L.; Leung, M. K.; Dai, C. A. *J. Polym. Sci. Part A Polym. Chem.* 2010, 48, 1607, each incorporated herein by reference in their entirety]. For example, cyanovinylene spacers (acceptor units) and thiophene derivatives (donors) have been employed successfully in the "D-A" approach to construct electropolymerizable polymers with band gaps ranging from 1.1 to 1.6 eV [Wagner, P.; Aubert P. H.; Lutsen, L.; Vanderzande, D. *Electrochem. Commun.* 2002, 4, 912; and Seshadri, V.; Sotzing, G. A. *Chem. Mater.* 2004, 16, 5644, each incorporated herein by reference in their entirety]. Another important parameter of a CP is its solubility in organic solvents, which would subsequently impact its processability by industrial techniques such as screen-printing, spin coating, roller coating, spray-coating and inkjet-printing. For instance, it is desirable to use soluble CPs for PVD manufacturing since blending of these polymers with a complementary acceptor is required to achieve bulk heterojunction. In fact, many non-conjugated polymers have been used in PVDs to overcome the solubility issue [Henckens, A.; Colladet, K.; Fourier, S.; Cleij, T, J.; Lutsen, L.; Gelan, J., Vanderzande, D. *Macromolecules* 2005, 38, 19; and van Breemen, A. J. J. M.; Issaris, A. C. J.; de Kok, M. M.; Van Der Borght, M. J. A. N.; Adriaensens, P. J.; Gelan, J. M. J. V.; Vanderzande, D. J. M. *Macromolecules* 1999, 32, 5728, each incorporated herein by reference in their entirety]. However, these non-conjugated polymers are unstable and prone to degradation in solid state, which can deteriorate the quality of the film and hence overall performance of the device.

Because of their extended π-electron system and inherent photophysical characteristics, CPs have been developed as optical sensors for toxic chemicals [McQuade, D. T.; Pullen, A. E.; Swager, T. M. *Chem. Rev.* 2000, 100, 2537; and Thomas III, S. W.; Joly, G. D.; Swager, T. M. *Chem. Rev.* 2007, 107, 1339, each incorporated herein by reference in their entirety] and biologically relevant molecules [Kim, I.-B.; Phillips, R.; Bunz, U. H. F. *Macromolecules* 2007, 40, 814; and Nambiar, S.; Yeow, J. T. W. *Biosens. Bioelectron.* 2011, 26, 1825, each incorporated herein by reference in their entirety]. Iodide plays an essential role in cell growth, neurological and metabolic activities, and function of thyroid gland in humans and animals [Martinez-Máñez, Sancenón, R. F. *Coord. Chem. Rev.* 2006, 250, 3081; Aldakov, D.; Palacios, M. A.; Anzenbacher Jr., P. *Chem. Mater.* 2005, 17, 5238; and Zimmermann, M.; Ito, Y.; Hess, S.; Fujieda, K.; Molinari, L. *Am. J. Clin. Nutr.* 2005, 81, 840]. Additionally, elemental iodine has been extensively used in producing synthetic dyes, radioactive medicine, radiocontrast agents and dietary supplements. However, excessive consumption or application of iodide can be irritating, corrosive, and toxic. Therefore, detecting iodide anions in pharmaceutical products, food, and biological samples such as urine at trace levels with high sensitivity and selectivity is crucial [Rhee, C. M.; Bhan, I.; Alexander E. K.; Brunelli, S. M. *Arch. Intern. Med.* 2012, 17, 153]. In spite of recent advances [Rambo, B. M.; Silver, E. S.; Bielawski, C. W.; Sessler, J. L. *Top Heterocycl Chem.* 2010, 25, 1, incorporated herein by reference in its entirety], there is a continuing need for iodide sensors.

In view of the forgoing, one objective of the present disclosure is to provide a copolymer capable of detecting iodide anions with high sensitivity and selectivity. Another aspect of the present disclosure is to provide a method for producing the copolymer, as well as a method for detecting a presence of iodide anions employing the copolymer.

BRIEF SUMMARY OF THE INVENTION

According to a first aspect, the present disclosure relates to a copolymer of Formula (I)

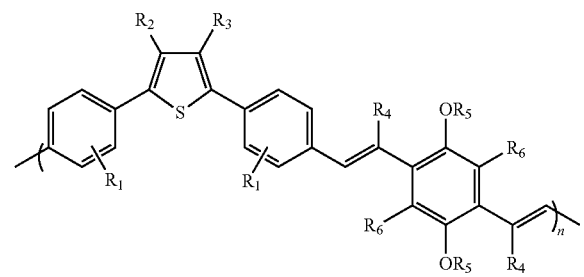

(I)

or a salt thereof, a solvate thereof, a tautomer thereof, a stereoisomer thereof, or a mixture thereof wherein (i) each $R_1$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano, (ii) $R_2$ and $R_3$ are independently selected from the group consisting of a hydrogen, an optionally substituted alkyl, an optionally substituted cycloalkyl, an optionally substituted arylalkyl, an optionally substituted alkoxy, an optionally substituted alkanoyl, and an optionally substituted aroyl, (iii) each $R_4$ is a hydrogen, or a cyano, (iv) each $R_5$ is selected from the group consisting of an optionally substituted alkyl, an optionally substituted cycloalkyl, an optionally substituted aryl, and an optionally substituted arylalkyl, (v) each $R_6$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano, and (vi) n is a positive integer in the range of 2-10,000.

In one embodiment, each $R_1$ and $R_6$ are a hydrogen, $R_2$ and $R_3$ are independently a hydrogen or an optionally substituted alkyl, and each $R_5$ is an optionally substituted alkyl.

In one embodiment, $R_2$ and $R_3$ are independently a hydrogen or hexyl, and each $R_5$ is 2-ethylhexyl or dodecyl.

In one embodiment, the copolymer has a formula selected from the group consisting of

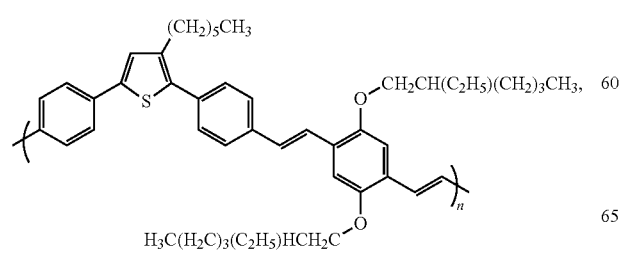

(II)

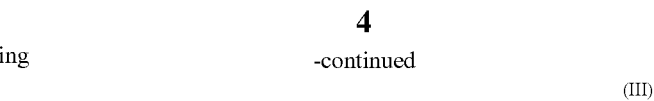

(III)

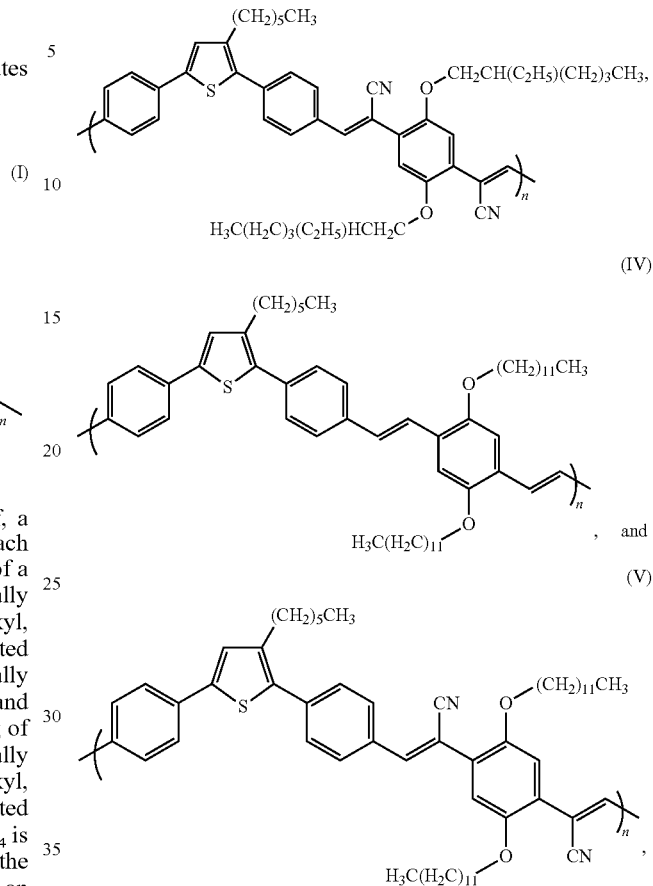

wherein n is a positive integer in the range of 2-10,000 for each of Formulae (II)-(V).

In one embodiment, the copolymer has an ultraviolet visible absorption with an absorption peak of 375-450 nm.

In one embodiment, the copolymer has a fluorescence emission peak of 520-590 nm upon excitation at a wavelength of 380-400 nm.

In one embodiment, the copolymer has a band gap energy of 1.8-2.7 eV.

According to a second aspect, the present disclosure relates to a method of producing the copolymer, wherein each $R_4$ is a hydrogen, the method comprising reacting a dialdehyde of Formula (VI)

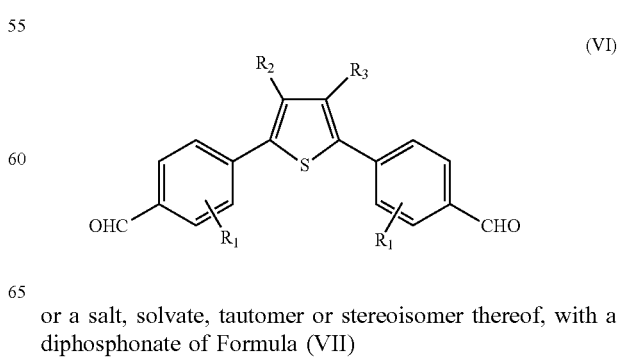

(VI)

or a salt, solvate, tautomer or stereoisomer thereof, with a diphosphonate of Formula (VII)

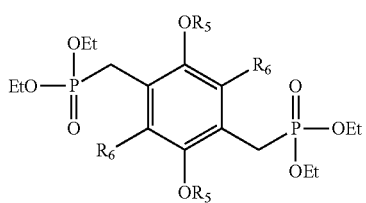

(VII)

or a salt, solvate, tautomer or stereoisomer thereof in the presence of a base to form the copolymer, wherein (i) each $R_1$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano, (ii) $R_2$ and $R_3$ are independently selected from the group consisting of a hydrogen, an optionally substituted alkyl, an optionally substituted cycloalkyl, an optionally substituted arylalkyl, an optionally substituted alkoxy, an optionally substituted alkanoyl, and an optionally substituted aroyl, (iii) each $R_5$ is selected from the group consisting of an optionally substituted alkyl, an optionally substituted cycloalkyl, an optionally substituted aryl, and an optionally substituted arylalkyl, and (iv) each $R_6$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano.

In one embodiment, a molar ratio of the dialdehyde to the diphosphonate is in the range of 1:2 to 2:1.

According to a third aspect, the present disclosure relates to a method of producing the copolymer, wherein each $R_4$ is a cyano, the method comprising reacting the dialdehyde of Formula (VI) or a salt, solvate, tautomer or stereoisomer thereof with a dinitrile of Formula (VIII)

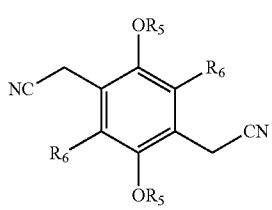

(VIII)

or a salt, solvate, tautomer or stereoisomer thereof in the presence of a base to form the copolymer, wherein (i) each $R_1$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano, (ii) $R_2$ and $R_3$ are independently selected from the group consisting of a hydrogen, an optionally substituted alkyl, an optionally substituted cycloalkyl, an optionally substituted arylalkyl, an optionally substituted alkoxy, an optionally substituted alkanoyl, and an optionally substituted aroyl, (iii) each $R_5$ is selected from the group consisting of an optionally substituted alkyl, an optionally substituted cycloalkyl, an option-ally substituted aryl, and an optionally substituted arylalkyl, and (iv) each $R_6$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano.

In one embodiment, a molar ratio of the dialdehyde to the dinitrile is in the range of 1:2 to 2:1.

According to a forth aspect, the present disclosure relates to a method of detecting $I^-$ anions in a fluid sample, comprising (i) contacting the fluid sample with the copolymer to form a mixture, and (ii) measuring an ultraviolet visible absorption profile of the mixture to determine a presence of $I^-$ anions in the fluid sample, wherein an ultraviolet visible absorption peak at 290-300 nm and/or 360-370 nm indicates the presence of $I^-$ anions.

In one embodiment, the fluid sample comprises greater than 10% v/v of water as a solvent and is at least one selected from the group consisting of contaminated water, a consumable good, and a bodily fluid.

In one embodiment, the copolymer is present in the mixture at a concentration of 1-1,000 nM.

In one embodiment, the copolymer is contacted with the fluid sample for 1 second to 24 hours.

In one embodiment, the method has an $I^-$ anion detection lower limit of 0.3-2.6 mM in the presence of one or more additional anions and counter cations.

In one embodiment, the one or more additional anions are at least one selected from the group consisting of $Br^-$, $Cl^-$, $F^-$, $NO_3^-$, and $CN^-$.

In one embodiment, the one or more additional counter cations are at least one selected from the group consisting of $Na^+$, $K^+$, $NH_4^+$, and $N[(CH_2)_3CH_3]_4^+$.

According to a fifth aspect, the present disclosure relates to a membrane comprising (i) a polymer selected from the group consisting of polyvinyl chloride, polystyrene, polyethylene, and poly(methyl methacrylate), and (ii) 0.1 to 75 wt % of the copolymer relative to a total weight of the membrane, wherein the copolymer is dispersed with the polymer.

In one embodiment, the membrane is further supported by a substrate.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
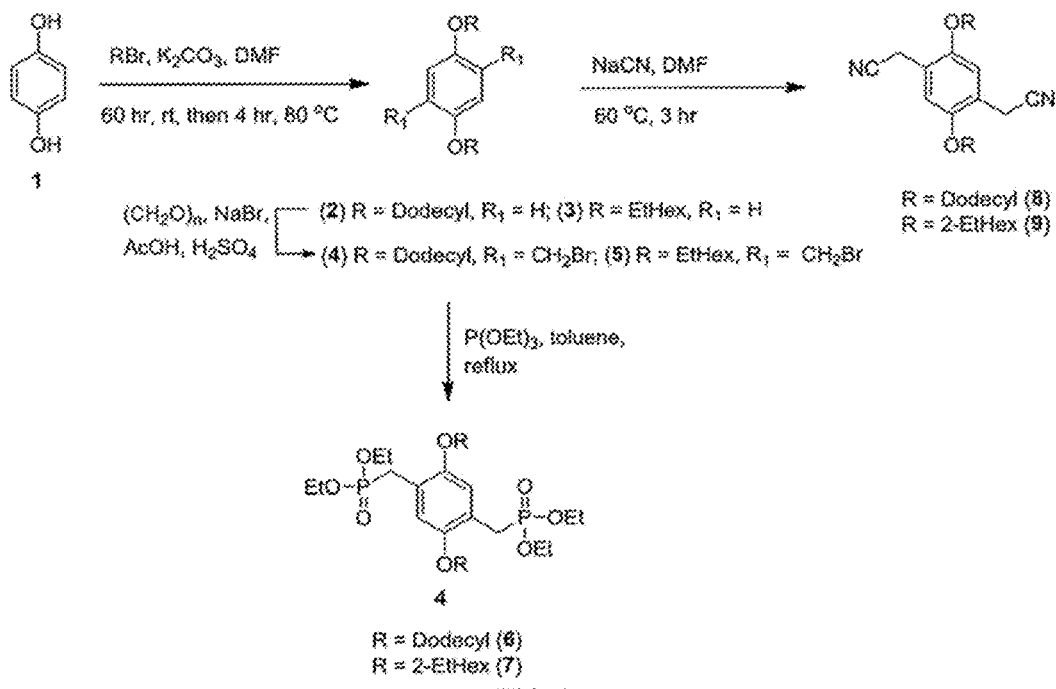
FIG. 1 are synthetic schemes for a diphosphonates of Formula (VII), wherein each $R_6$ is a hydrogen, and each $R_5$ is dodecyl (compound 6), or 2-ethylhexyl (compound 7), and for a dinitrile of Formula (VIII), wherein each $R_6$ is a hydrogen, and each $R_5$ is dodecyl (compound 8), or 2-ethylhexyl (compound 9).

Embodiments of the present disclosure will now be described more fully hereinafter with reference to the accompanying drawings, in which some, but not all embodiments of the disclosure are shown.

The present disclosure will be better understood with reference to the following definitions.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those skilled in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, and the like can all be present in the compounds, and all such stable isomers are contemplated in the present disclosure. Cis- and trans- (or E- and Z-) stereoisomers of the compounds of the present disclosure wherein rotation around the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

The present disclosure is further intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}$C and $^{14}$C, isotopes of nitrogen include $^{15}$N, isotopes of oxygen include $^{17}$O and $^{18}$O, and isotopes of sulfur include $^{33}$S, $^{34}$S and $^{36}$S. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, aubstituted aralkanoylamino, thiol, alkylthio, arylthio, arylalkylthio, alkylthiono, arylthiono, aryalkylthiono, alkyl sulfonyl, aryl sulfonyl, arylalkylsulfonyl, sulfonamide (e.g. —SO$_2$NH$_2$), substituted sulfonamide, nitro, cyano, carboxy, carbamyl (e.g. —CONH$_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like.

As used herein, the term "alkyl" unless otherwise specified refers to both branched and straight chain saturated aliphatic primary, secondary, and/or tertiary hydrocarbons of typically $C_1$ to $C_{20}$, preferably $C_6$-$C_{18}$, more preferably $C_{10}$-$C_{16}$, for example $C_1$, $C_2$, $C_3$, $C_4$, $C_5$, $C_6$, $C_7$, $C_8$, $C_9$, $C_{10}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl. As used herein, the term optionally includes substituted alkyl groups. Exemplary moieties with which the alkyl group can be substituted may be selected from the group including, but not limited to, hydroxyl, amino, alkylamino, arylamino, alkoxy, aryloxy, nitro, cyano, sulfonic acid, sulfate, phosphonic acid, phosphate, halo, or phosphonate or mixtures thereof. The substituted moiety may be either protected or unprotected as necessary, and as known to those skilled in the art.

The term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "arylalkyl", as used herein, refers to a straight or branched chain alkyl moiety having 1 to 8 carbon atoms that is substituted by an aryl group as defined herein, and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

As used herein, the term "aryl" unless otherwise specified refers to functional groups or substituents derived from an aromatic ring including, but not limited to, phenyl, biphenyl, napthyl, thienyl, and indolyl. As used herein, the term optionally includes both substituted and unsubstituted moieties. Exemplary moieties with which the aryl group can be substituted may be selected from the group including, but not limited to, hydroxyl, amino, alkylamino, arylamino, alkoxy, aryloxy, nitro, cyano, sulfonic acid, sulfate, phosphonic acid, phosphate or phosphonate or mixtures thereof. The substituted moiety may be either protected or unprotected as necessary, and as known to those skilled in the art.

The term "alkoxy" refers to a straight or branched chain alkoxy including, but not limited to, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy.

The term "alkanoyl" refers to an alkyl group of specified number of carbon atoms that is bound to an oxygen atom through a double bond. Exemplary alkanoyl groups include, but are not limited to, formyl, acetyl, propanoyl, butyryl, and hexanoyl.

The term "aroyl" as used in this disclosure refers to an aromatic carboxylic acyl group includes, for example, benzoyl, 1-naphthoyl, and 2-naphthoyl.

The term "halogen", as used herein, means fluoro, chloro, bromo and iodo.

According to one aspect, the present disclosure relates to a copolymer of Formula (I)

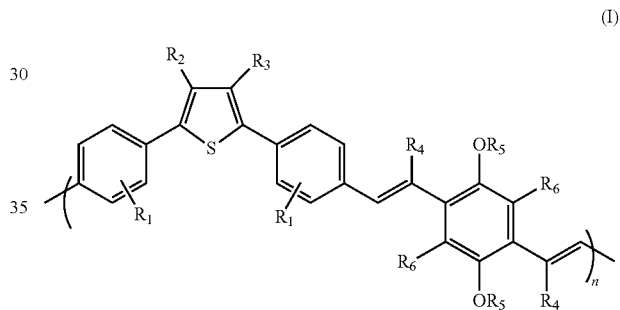

(I)

or a salt thereof, a solvate thereof, a tautomer thereof, a stereoisomer thereof, or a mixture thereof wherein (i) each $R_1$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano, (ii) $R_2$ and $R_3$ are independently selected from the group consisting of a hydrogen, an optionally substituted alkyl, an optionally substituted cycloalkyl, an optionally substituted arylalkyl, an optionally substituted alkoxy, an optionally substituted alkanoyl, and an optionally substituted aroyl, (iii) each $R_4$ is a hydrogen, or a cyano, (iv) each $R_5$ is selected from the group consisting of an optionally substituted alkyl, an optionally substituted cycloalkyl, an optionally substituted aryl, and an optionally substituted arylalkyl, (v) each $R_6$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano, and (vi) n is a positive integer in the range of 2-10,000.

As described herein, the term "repeat unit" or "repeating unit" refers to a part of the polymer or resin whose repetition would produce the complete polymer chain (including or excluding the end groups) by linking the repeating units together successively along the chain. Monomers are molecules which can undergo polymerization, thereby contributing constitutional repeating units to the structures of a macromolecule or polymer. The process by which monomers combine end to end to form a polymer is referred to herein as "polymerization" or "polycondensation". As used herein a "copolymer" refers to a polymer derived from more than one species of monomer and are obtained by "copolymerization" of more than one species of monomer. Copolymers obtained by copolymerization of two monomer and/or oligomer species may be termed bipolymers, those obtained from three monomers may be termed terpolymers and those obtained from four monomers may be termed quarterpolymers, etc. In some embodiments, the copolymer of the present disclosure is a terpolymer, for example a terpolymer obtained from reaction between a dialdehyde and a mixture of two diphosphonates or two dinitriles. In a preferred embodiment, the copolymer of the present disclosure is a bipolymer.

The term "degree of polymerization" refers to the number of repeating units in a polymer. In a preferred embodiment, degree of polymerization n is a positive integer in the range of 2-10,000, preferably 3-1,000, preferably 4-500, preferably 5-100, preferably 6-90, preferably 7-80, preferably 8-70, preferably 9-60, preferably 10-50, preferably 11-40, preferably 12-30, preferably 13-25, preferably 14-20. It is equally envisaged that values for n may fall outside of these ranges and still provide suitable copolymers of Formula (I). In a preferred embodiment, the copolymer of the present disclosure may have a wide molecular weight distribution. In one embodiment, the copolymer of the present disclosure has an average molecular weight of 2-100 kDa, preferably 5-80 kDa, preferably 10-60 kDa, preferably 15-40 kDa, preferably 18-35 kDa, preferably 20-30 kDa.

In one or more embodiments, each $R_1$ and $R_6$ are a hydrogen. In one or more embodiments, $R_2$ and $R_3$ are independently a hydrogen or an optionally substituted alkyl. Within the same repeating unit, each $R_5$ may be the same or may be different groups. In one or more embodiments, each $R_5$ is an optionally substituted alkyl. In one or more embodiments, $R_2$ and $R_3$ are the same. In one or more embodiments, $R_2$ and $R_3$ are different.

In one or more embodiments, $R_2$ and $R_3$ are independently a hydrogen or a $C_4$ to $C_8$ alkyl group, preferably a $C_5$ to $C_7$ alkyl group, more preferably a $C_6$ alkyl group, most preferably hexyl, and each $R_5$ is a $C_6$ to $C_{14}$ alkyl group, preferably a $C_7$ to $C_{13}$ alkyl group, more preferably a $C_8$ to $C_{12}$ alkyl group, most preferably 2-ethylhexyl or dodecyl.

In one or more embodiments, the copolymer has a formula selected from the group consisting of

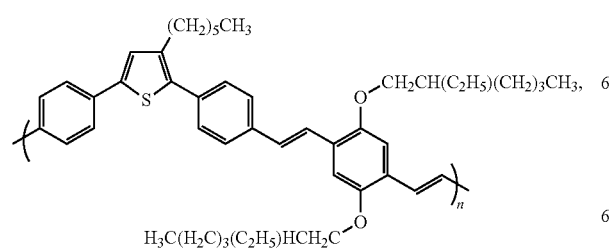

(II)

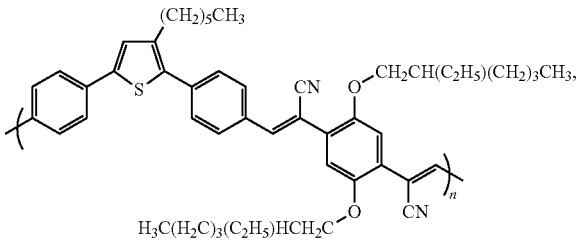

(III)

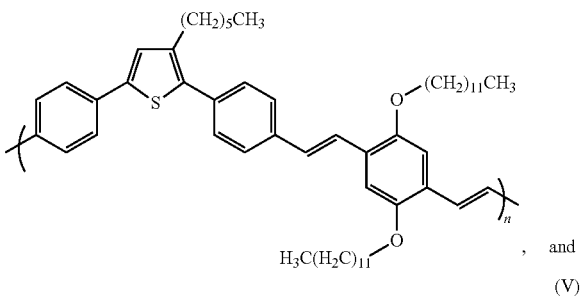

(IV)

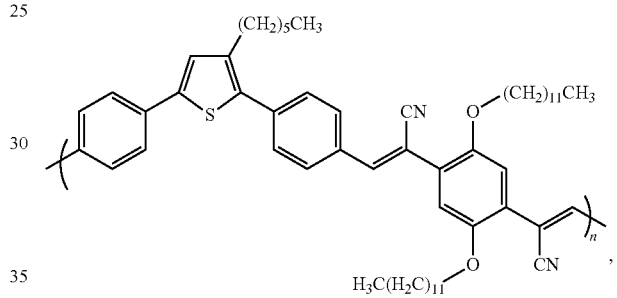

(V)

wherein n is a positive integer in the range of 2-10,000, preferably 3-1,000, preferably 4-500, preferably 5-100, preferably 6-90, preferably 7-80, preferably 8-70, preferably 9-60, preferably 10-50, preferably 11-40, preferably 12-30, preferably 13-25, preferably 14-20, for each of Formulae (II)-(V).

There are in principle a relatively large number of different reactions for the formation of alkene (C=C) bond suitable for the purpose of current disclosure, which include, but are not limited to, Wittig reaction, Peterson olefination, Barton-Kellogg reaction, McMurry reaction, Ramberg-Backlund rearrangement, and Olefin metathesis. Horner-Wadsworth-Emmons (HWE) reaction is a more specific example of Wittig reaction, which involves reacting phosphonates with aldehydes (or ketones) under basic conditions to produce corresponding (E)-alkene compounds. In a preferred embodiment, reactions of HWE type leads to the copolymer of Formula (I) wherein each $R_4$ is a hydrogen. Knoevenagel condensation, which is a modification of the aldol condensation, converts an aldehyde or ketone and a reactant with active hydrogens to an olefin in the presence of a basic catalyst. In a preferred embodiment, reactions of Knoevenagel type leads to the copolymer of Formula (I) wherein each $R_4$ is a cyano.

According to another aspect, the present disclosure relates to a method of producing the copolymer of the first aspect, wherein each $R_4$ is a hydrogen, the method comprising reacting a dialdehyde of Formula (VI)

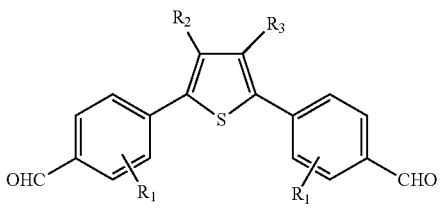

(VI)

or a salt, solvate, tautomer or stereoisomer thereof, with a diphosphonate of Formula (VII)

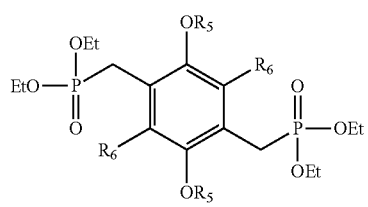

(VII)

or a salt, solvate, tautomer or stereoisomer thereof in the presence of a base to form the copolymer, wherein (i) each $R_1$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano, (ii) $R_2$ and $R_3$ are independently selected from the group consisting of a hydrogen, an optionally substituted alkyl, an optionally substituted cycloalkyl, an optionally substituted arylalkyl, an optionally substituted alkoxy, an optionally substituted alkanoyl, and an optionally substituted aroyl, (iii) each $R_5$ is selected from the group consisting of an optionally substituted alkyl, an optionally substituted cycloalkyl, an optionally substituted aryl, and an optionally substituted arylalkyl, and (iv) each $R_6$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano.

In a preferred embodiment, reacting the dialdehyde with the diphosphonate in the presence of a base to form the copolymer wherein each $R_4$ is a hydrogen is performed in a polar aprotic solvent (e.g. tetrahydrofuran, dimethylformamide, acetonitrile) under agitation, preferably a magnetic stirrer at a temperature of 20-150° C., preferably 40-140° C., preferably 60-130° C., preferably 80-120° C., or about 100° C. for up to 48 hours, preferably 2-44 hours, preferably 8-38 hours, preferably 12-32 hours, preferably 18-30 hours, or about 24 hours. In a preferred embodiment, the reaction is performed at a concentration of the dialdehyde in the range of 0.1-1,000 mM, preferably 0.5-500 mM, preferably 1-100 mM, preferably 10-50 mM, preferably 20-40 mM. In a preferred embodiment, the reaction is performed at a concentration of the diphosphonate in the range of 0.1-1,000 mM, preferably 0.5-500 mM, preferably 1-100 mM, preferably 10-50 mM, preferably 20-40 mM. The base may be present at a concentration in the range of 1-1000 mM, preferably 10-500 mM, preferably 50-250 mM, preferably 100-200 mM. Exemplary bases that may be suitable for the reaction include, but are not limited to, sodium tert-butoxide, potassium tert-butoxide, 1,8-diazabicycloundec-7-ene, 1,5-diazabicyclo(4.3.0)non-5-ene, n-butyllithium, tert-butyllithium, lithium diisopropylamide, sodium hydride, potassium hydride, sodium methoxide, and sodium carbonate, preferably sodium tert-butoxide is employed. In a preferred embodiment, a molar ratio of the dialdehyde to the diphosphonate is in the range of 1:3 to 3:1, preferably 1:2 to 2:1, preferably 2:3 to 3:2, or about 1:1. In a preferred embodiment, a molar ratio of the dialdehyde to the base is in the range of 1:1 to 1:30, preferably 1:2 to 1:20, preferably 1:3 to 1:10, preferably 1:4 to 1:8, or about 1:5.

In a preferred embodiment, the copolymer is collected as a solid that may be separated (filtered off) from the aforementioned reaction, washed in methanol, iso-propanol, tetrahydrofuran, and/or hexanes, and then filtered and dried. In a preferred embodiment, the aforementioned reaction forming the copolymer of Formula (I) wherein each $R_4$ is a hydrogen has a product yield of at least 50%, preferably at least 60%, preferably at least 65%, preferably at least 70%, preferably at least 75%, preferably at least 80%, preferably at least 85%, preferably at least 90%. The product yield is calculated as (mass of product/mass of reactants, i.e., dialdehyde+diphosphonate)×100%.

According to another aspect, the present disclosure relates to a method of producing the copolymer, wherein each $R_4$ is a cyano, the method comprising reacting the dialdehyde of Formula (VI) or a salt, solvate, tautomer or stereoisomer thereof with a dinitrile of Formula (VIII)

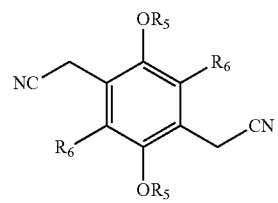

(VIII)

or a salt, solvate, tautomer or stereoisomer thereof in the presence of a base to form the copolymer, wherein (i) each $R_1$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano, (ii) $R_2$ and $R_3$ are independently selected from the group consisting of a hydrogen, an optionally substituted alkyl, an optionally substituted cycloalkyl, an optionally substituted arylalkyl, an optionally substituted alkoxy, an optionally substituted alkanoyl, and an optionally substituted aroyl, (iii) each $R_5$ is selected from the group consisting of an optionally substituted alkyl, an optionally substituted cycloalkyl, an optionally substituted aryl, and an optionally substituted arylalkyl, and (iv) each $R_6$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano.

In a preferred embodiment, reacting the dialdehyde with the dinitrile in the presence of a base to form the copolymer wherein each $R_4$ is a cyano is performed in a polar aprotic solvent (e.g. tetrahydrofuran, dimethylformamide, acetonitrile) under agitation, preferably a magnetic stirrer at a temperature of 20-120° C., preferably 30-110° C., preferably 40-100° C., preferably 50-90° C., preferably 60-80° C., or about 70° C. for up to 24 hours, preferably 2-20 hours, preferably 4-18 hours, preferably 6-16 hours, preferably 8-14 hours, or about 12 hours. In a preferred embodiment, the reaction is performed at a concentration of the dialdehyde in the range of 0.1-1,000 mM, preferably 0.5-500 mM, preferably 1-100 mM, preferably 10-50 mM, preferably 20-40 mM. In a preferred embodiment, the reaction is performed at a concentration of the dinitrile in the range of 0.1-1,000 mM, preferably 0.5-500 mM, preferably 1-100 mM, preferably 10-50 mM, preferably 20-40 mM. The base may be present at a concentration in the range of 1-1000 mM, preferably 10-500 mM, preferably 50-250 mM, preferably 80-150 mM. Exemplary bases that may be suitable for the reaction include, but are not limited to, sodium tert-butoxide, potassium tert-butoxide, 1,8-diazabicycloundec-7-ene, 1,5-diazabicyclo(4.3.0)non-5-ene, n-butyllithium, tert-butyllithium, lithium diisopropylamide, sodium hydride, potassium hydride, sodium methoxide, and sodium carbonate, preferably sodium tert-butoxide is employed. In a preferred embodiment, a molar ratio of the dialdehyde to the dinitrile is in the range of 1:3 to 3:1, preferably 1:2 to 2:1, preferably 2:3 to 3:2, or about 1:1. In a preferred embodiment, a molar ratio of the dialdehyde to the base is in the range of 3:1 to 1:20, preferably 2:1 to 1:10, preferably 1:1 to 1:5, preferably 1:2 to 1:4, or about 1:3.

In a preferred embodiment, the copolymer is collected as a solid that may be separated (filtered off) from the aforementioned reaction, washed in methanol, treated with an acid (e.g. acetic acid, hydrochloric acid), and then filtered and dried. In a preferred embodiment, the aforementioned reaction forming the copolymer of Formula (I) wherein each $R_4$ is a cyano has a product yield of at least 50%, preferably at least 60%, preferably at least 65%, preferably at least 70%, preferably at least 75%, preferably at least 80%, preferably at least 85%. The product yield is calculated as (mass of product/mass of reactants, i.e., dialdehyde+dinitrile)×100%.

The starting monomers used in the aforementioned methods including dialdehydes, diphosphonates and dinitriles may be commercially available or prepared in-house according to methods known to one of ordinary skill in the art. For example, details regarding the synthetic procedures for the diphosphate of Formula (VII) and dinitriles of Formula (VIII) may be found, e.g. in Egbe, D. A. M.; Ulbricht, C.; Orgis, T.; Carbonnier, B.; Kietzke, T.; Peip, M.; Manuela, M. M.; Gericke, M.; Birckner, E.; Pakula, T.; Neher, D.; Grummt, U. W. Chem. Mater. 2005, 17, 6022; and Yang, J.; Liu, X.; Huang, C.; Zhou, C.; Li, Y.; Zhu, D. Chemphyschem 2010, 11, 659; and Thompson, B. C.; Kim, Y. G.; McCarley, T. D.; Reynolds, J. R. J. Am. Chem. Soc. 2006, 128, 12714—incorporated herein by reference in their entirety. For another example, the dialdehyde of Formula (VI) may be prepared by the Suzuki-Miyaura method as follows. A boronic ester of Formula (VI-i)

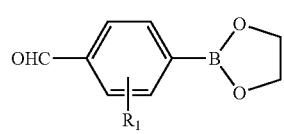

may be mixed with a proper 2,5-dibromothiophene of Formula (VI-ii)

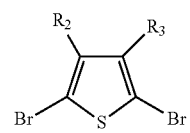

in the presence of a base (e.g. sodium carbonate, potassium carbonate, sodium hydroxide, potassium hydroxide, sodium tert-butoxide, potassium tert-butoxide) and a catalyst (e.g. [1,1'-bis(diphenylphosphino)ferrocene]dichloropalladium (II) [PdCl$_2$(dppf)], palladium-tetrakis(triphenylphosphine) [Pd(PPh$_3$)$_4$], palladium(II) acetate [Pd(OAc)$_2$], bis(dibenzylideneacetone)palladium [Pd(dba)$_2$]) in a protic solvent (e.g. water, methanol, ethanol, dioxane, tetrahydrofuran), thereby forming a mixture. A concentration of boronic ester of Formula (VI-i) in the mixture may be in the range of 0.1-4 M, 0.4-2 M, or 0.8-1.0 M. A concentration of 2,5-dibromothiophene of Formula (VI-ii) in the mixture may be in the range of 0.05-2 M, 0.1-1 M, or 0.2-0.6 M. A concentration of base in the mixture may be in the range of 0.1-4 M, 0.5-2 M, or 1.0-1.5 M. A concentration of catalyst in the mixture may be in the range of 0.005-0.2 M, 0.01-0.1 M, or 0.02-0.06 M. A molar ratio of the boronic ester to the 2,5-dibromothiophene may be in the range of 1:1 to 5:1, or 2:1 to 3:1. A molar ratio of the boronic ester to the base may be in the range of 1:1 to 1:4, or 1:2 to 1:3. A molar ratio of the boronic ester to the catalyst may be in the range of 100:1 to 5:1, 50:1 to 10:1, or 40:1 to 20:1. The mixture may be agitated and/or heated to a temperature range of 50-200° C., 60-150° C., or 70-120° C. by an oil-bath, a sand-bath, or preferably a microwave for 5 minutes to 6 hours, 10 minutes to 3 hours, or 15 minutes to 1 hour to form a final reaction mixture. Subsequently, the dialdehyde of Formula (VI) may be isolated and purified from the final reaction mixture using methods known one skilled in the art such as filtration, work-up, extraction with organic solvents, distillation, crystallization, column chromatography, and high-performance liquid chromatography (HPLC). A yield of the dialdehyde may be at least 50%, preferably at least 60%, preferably at least 70%, preferably at least 80%, preferably at least 85%, preferably at least 90% by mole relative to the total mole of starting material 2,5-dibromothiophene of Formula (VI-ii). Methods of agitating a reaction mixture include, without limitation, using an agitator, a vortexer, a rotary shaker, a magnetic stirrer, a centrifugal mixer, an overhead stirrer, an ultrasonic probe, or placing the reaction mixture in an ultrasonic bath.

The present disclosure is intended to include a mixed copolymer formed by employing more than one dialdehyde of Formula (VI) with different substitutions at $R_1$, $R_2$, and/or $R_3$, and/or more than one diphosphonate of Formula (VII) with different substitutions at $R_5$ and/or $R_6$ in a polycondensation. The present disclosure is also intended to include a mixed copolymer formed by employing more than one dialdehyde of Formula (VI) with different substitutions at $R_1$, $R_2$, and/or $R_3$, and/or more than one dinitrile of Formula (VIII) with different substitutions at $R_5$ and/or $R_6$ in a polycondensation. An exemplary structure of the formed mixed copolymer may be represented by Formula (IX)

(IX)

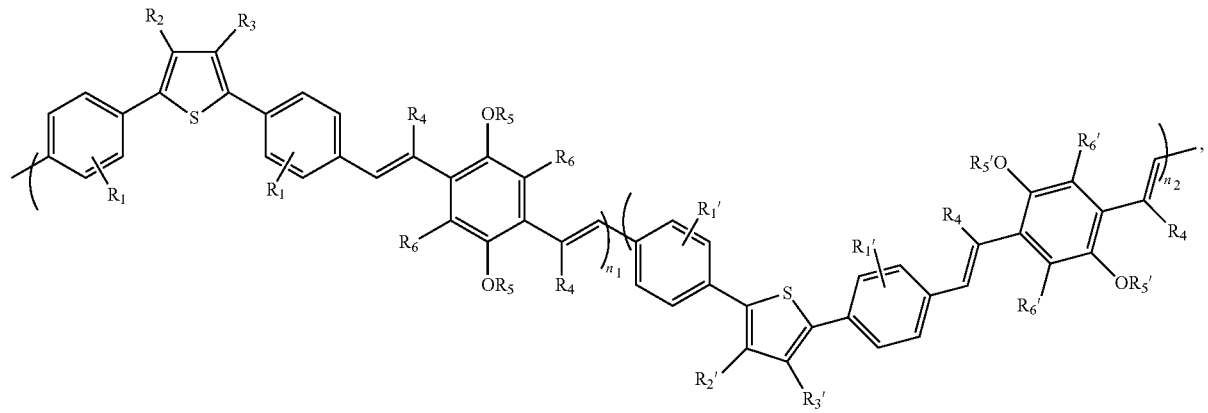

wherein (i) each $R_1$ and $R_1'$ are independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano, (ii) $R_2$, $R_2'$, $R_3$, and $R_3'$ are independently selected from the group consisting of a hydrogen, an optionally substituted alkyl, an optionally substituted cycloalkyl, an optionally substituted arylalkyl, an optionally substituted alkoxy, an optionally substituted alkanoyl, and an optionally substituted aroyl, (iii) each $R_4$ is a hydrogen, or a cyano, (iv) each $R_5$ and $R_5'$ are selected from the group consisting of an optionally substituted alkyl, an optionally substituted cycloalkyl, an optionally substituted aryl, and an optionally substituted arylalkyl, (v) each $R_6$ and $R_6'$ are independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano, (vi) $n_1$ and $n_2$ are independently a positive integer in the range of 2-10,000, and (vii) $R_1 \neq R_1'$, $R_2 \neq R_2'$, $R_3 \neq R_3'$, $R_5 \neq R_5'$, and/or $R_6 \neq R_6'$.

The copolymer may be a block copolymer, an alternating copolymer, a periodic copolymer, a gradient copolymer, or a statistical copolymer. Block copolymers comprise two or more homopolymer subunits linked by covalent bonds. The union of the homopolymer subunits may require an intermediate non-repeating subunit, known as a junction block. Block copolymers with two or three distinct blocks are called diblock copolymers and triblock copolymers, respectively. Statistical copolymers are copolymers in which the sequence of monomer residues follows a statistical rule. That is, the probability of finding a particular monomer residue at a particular point in the chain is equal to the mole fraction of that monomer residue in the chain. The statistical copolymer may be referred to as a truly random copolymer. Periodic copolymers have the monomers arranged in a repeating sequence. In an embodiment where either only one type of diphosphonate or dinitrile is present as the first monomer, only one type of dialdehyde is present as the second monomer, and the mole ratio of the first monomer to the second monomer is about 1:1, the copolymer is an alternating copolymer with regular alternating A and B (e.g., $(A-B)_n$), where A represents the first monomer and B represents the second monomer. In another embodiment, the copolymer may be a gradient copolymer which exhibits a gradual change in composition along the polymer chain from mostly A units to mostly B units.

In certain embodiments, structural and photo-physical evaluations may be performed for the copolymers of Formula (I) of the present disclosure. Molecular structures of disclosed copolymers may be characterized by spectroscopic techniques such as infrared (IR), mass spectrometry (MS), nuclear magnetic resonance (NMR) studies (see examples 2-5) or other known instrumentation common to those of ordinary skill in the art. Photo-physical properties of disclosed copolymers may be assessed by other spectroscopic tools such as ultraviolet-visible (UV-vis) spectroscopy and fluorescence spectroscopy (see example 7). Stock solutions or thin films of the copolymers may be prepared for UV-vis and fluorescence studies. A thin film of the copolymers may be produced by depositing the copolymer to a substrate via various techniques including, without limitation, chemical vapor deposition, atomic layer deposition, chemical solution deposition by dip coating, spin coating or spraying, Langmuir-Blodgett method, sputter deposition, cathodic arc deposition, pulsed laser deposition, or thermal evaporation method. In a preferred embodiment, the thin film of the disclosed copolymer is produced by chemical deposition by spin coating or thermal evaporation method. Exemplary substrates include quartz, silicon wafer, fluorine doped tin oxide coated glass, indium tin oxide (ITO) coated glass, ITO coated polyethylene terephthalate (PET) film, gold coated glass, aluminum oxide, titanium oxide, and strontium titanate. In some embodiments, a thin film of the copolymer has a thickness of 10 nm to 100 um, 50 nm to 50 um, 100 nm to 10 um, 500 nm to 5 um, or 1 um to 3 um.

As used herein, UV-vis spectroscopy or UV-vis spectrophotometry refers to absorption spectroscopy or reflectance spectroscopy in the ultraviolet-visible spectral region. This means it uses light in the visible and adjacent (near-UV and near-infrared) ranges. The absorption or reflectance in the visible range directly affects the perceived color of the chemicals involved. In this region of the electromagnetic spectrum, molecules undergo electronic transitions. Molecules containing π-electrons or non-bonding electrons (n-electrons) can absorb the energy in the form of ultraviolet or visible light to excite these electrons to higher antibonding molecular orbitals. The more easily excited electrons (i.e. the lower the energy gap between the HOMO and the LUMO), the longer the wavelength of light it can absorb. This technique is complementary to fluorescence spectroscopy, in that fluorescence deals with transitions from the excited state to the ground state, while absorption measures transitions from the ground state to the excited state. In a preferred embodiment, the copolymer of Formula (I) has an ultraviolet visible absorption with an absorption peak of 330-480 nm, preferably 350-460 nm, preferably 375-450 nm, preferably 380-445 nm, preferably 390-440 nm, preferably 400-430 nm. In a more preferred embodiment, a thin film of the copolymer of Formula (I) has an ultraviolet visible absorption with an absorption peak of 375-450 nm, preferably 380-445 nm, preferably 390-440 nm, preferably 400-430 nm. In some embodiments, copolymers wherein each $R_4$ is a hydrogen have absorption peaks with a longer wavelength relative to those of copolymers wherein each $R_4$ is a cyano group by at least 10 nm, 20 nm, 30 nm, 40 nm, 50 nm, 60 nm, or 70 nm. In at least one embodiment, a bathochromic shift (or red shift) is observed for the absorption of the copolymer described herein by going from solution to thin film state. Depending on the aggregation of the copolymer in the thin film state, the aforementioned bathochromic shift may be at least 5 nm, 8 nm, 10 nm, 15 nm, 20 nm, 30 nm, 40 nm, or 50 nm.

As used herein, fluorescence is the emission of light by a substance that has absorbed light or other electromagnetic radiation. It is a form of luminescence. However, unlike phosphorescence, where the substance would continue to glow and emit light for some time after the radiation source has been turned off, fluorescent materials would cease to glow immediately upon removal of the excitation source. Hence, it is not a persistent phenomenon. Fluorescence occurs when an orbital electron of a molecule, atom, or nanostructure relaxes to its ground state by emitting a photon from an excited singlet state. In most cases, the emitted light has a longer wavelength, and therefore lower energy, than the absorbed radiation in a phenomenon known as the Stokes shift. Many molecules that fluoresce are conjugated systems. In a preferred embodiment, the copolymer of Formula (I) has a fluorescence emission peak of 500-620 nm, preferably 510-600 nm, preferably 520-590 nm, preferably 530-580 nm, preferably 540-570 nm, preferably 550-560 nm at an excitation wavelength of 370-410 nm, preferably 380-400 nm, preferably 382-398 nm, preferably 384-396 nm, preferably 386-394 nm, preferably 388-392 nm, or about 390 nm. In a more preferred embodiment, a thin film of the copolymer of Formula (I) has a fluorescence emission peak of 520-590 nm, preferably 530-580 nm, preferably 540-570 nm, preferably 550-560 nm at an excitation wavelength of 370-410 nm, preferably 380-400 nm, preferably 382-398 nm, preferably 384-396 nm, preferably 386-394 nm, preferably 388-392 nm, or about 390 nm. In some embodiments, copolymers wherein each $R_4$ is a hydrogen have emission peaks with a shorter wavelength relative to those of copolymers wherein each $R_4$ is a cyano group by at least 10 nm, 20 nm, 30 nm, 40 nm, or 50 nm. In some embodiments, the copolymer of Formula (I) has a Stokes shift of at least 30 nm, 40 nm, 50 nm, 60 nm, 70 nm, 80 nm or 90 nm, which is calculated based on the difference between emission and excitation peaks. This large Stokes shift is advantageous as it reduces overlap between the emission profile and background excitation light and thus offers fluorescence images of higher resolution. Additionally, an effective excitation wavelength of the copolymers described herein that is within the visible light region can prevent potential damages to living biological samples and synthetic polymers.

As used herein, quantum yield (Φ) refers to the fluorescence quantum yield and gives the efficiency of the fluorescence process. It is defined as the ratio of the number of photons emitted to the number of photons absorbed. The maximum fluorescence quantum yield is 1.0 (100%); wherein each photon absorbed results in a photon emitted. An alternative way to define the quantum yield of fluorescence is by the rate of excited state decay. In a preferred embodiment, the copolymer of Formula (I) has a quantum yield in a range of 0.05-0.9, preferably 0.1-0.8, preferably 0.2-0.7, preferably 0.3-0.6, preferably 0.4-0.5 for its fluorescence emission peak of 500-620 nm, preferably 510-600 nm, preferably 520-590 nm, preferably 530-580 nm, preferably 540-570 nm, preferably 550-560 nm at an excitation wavelength of 370-410 nm, preferably 380-400 nm, preferably 382-398 nm, preferably 384-396 nm, preferably 386-394 nm, preferably 388-392 nm, or about 390 nm.

As defined herein, conjugated polymers are polymers which contain mainly $sp^2$-hybridized (or also sp-hybridized) carbon atoms in the main chain, which may also be replaced by appropriate heteroatoms. In the simplest case, this means the presence of alternating double and single bonds in the main chain. Naturally occurring defects or minor impurities which lead to interruptions to the conjugation do not invalidate the term "conjugated polymers". Furthermore, a polymer in which, for example, thiophene units such as the diphenylthiophene of Formula (I) or other such units and/or particular heterocycles (i.e. conjugation via S, O or N atoms) are present in the main chain is likewise described as conjugated in the present disclosure. On the other hand, units such as simple (thio)ether bridges, ester linkages, amide or imide linkages would be unambiguously defined as non-conjugated segments. In one or more embodiments, the copolymer disclosed herein is a conjugated polymer.

As used herein, band gap energy ($E_g$), band gap, and/or energy gap refers to an energy range in a solid where no electron states can exist. In graphs of the electronic band structure of solids, the band gap generally refers to the energy difference (in electron volts) between the top of the valence band and the bottom of the conduction band in insulators and/or semiconductors. It is generally the energy required to promote a valence electron bound to an atom to become a conduction electron, which is free to move within the crystal lattice and serve as a charge carrier to conduct electric current. Optoelectronic materials such as conjugated polymers are generally classified according to their band gap, which is closely related to the HOMO/LUMO gap in chemistry. Band gap energies for copolymers described herein may be obtained using optical spectroscopies, e.g. UV-vis spectroscopy and/or electrochemical measurements, e.g. cyclic voltammetry (CV) and differential pulse voltammetry (DPV). In one or more embodiments, the copolymer has a band gap energy of 1.8-2.7 eV, 1.9-2.6 eV, 2.0-2.5 eV, 2.1-2.4 eV, or 2.2-2.3 eV.

According to another aspect, the present disclosure relates to a method of detecting I⁻ ions in a fluid sample, comprising (i) contacting the fluid sample with the copolymer to form a mixture, and (ii) measuring an ultraviolet visible absorption profile of the mixture to determine a presence of I⁻ ions in the fluid sample, wherein an ultraviolet visible absorption peak at 290-300 nm and/or 360-370 nm indicates the presence of I⁻ anions.

In terms of the present disclosure, the fluid sample may be taken from any suitable source where the presence of I⁻ anions is to be determined, for instance, from food, pharmaceuticals, water sources, plants, animals, bodily fluids, tissues samples, environmental samples (e.g. air, water, soil, plants), or the like. Non-limiting examples of water sources include surface water that collects on the ground or in a stream, aquifer, river, lake, reservoir or ocean, ground water that is obtained by drilling wells, run-off, industrial water, industrial effluent water, tap water, public water storage towers, public recreational pools and/or bottled water. In other embodiments, the fluid sample may be a bodily fluid (e.g. lymph, saliva, urine, whole blood, dried blood, blood plasma, milk, breast secretions). It is further envisaged that the method of the present disclosure may be used for detecting $I^-$ ions in applications including, but not limited to, water quality monitoring, environmental pollution control, pharmaceutical and cosmetics industry quality control, food quality control, agriculture and fishery industries, medical diagnosis, industrial waste production, waste water treatment, and as a research tool. The method and compounds of the present disclosure may advantageously be used for detecting $I^-$ ions that are of environmental or human health concerns. In a preferred embodiment, the fluid sample is at least one selected from the group consisting of contaminated water, a consumable good, and a bodily fluid.

In a preferred embodiment, the fluid sample is an aqueous sample comprising greater than 10% v/v of water, preferably 10-99% v/v, preferably 20-80% v/v, preferably 30-75% v/v of water. In certain embodiments, the fluid sample may further comprise up to 90% v/v of an organic solvent including, but not limited to, tetrahydrofuran, acetonitrile, methanol, ethanol, n-propanol, isopropanol, n-butanol and mixtures thereof as secondary solvents, preferably tetrahydrofuran. In a preferred embodiment, the fluid sample may comprise 5-90% v/v of tetrahydrofuran, preferably 10-80% v/v, preferably 15-60% v/v, preferably 20-50% v/v of tetrahydrofuran.

In terms of the present disclosure, the method and contacting may be carried out in tanks, containers, or small scale applications in both batch mode and/or fixed-bed or column mode. In an exemplary batch mode, the copolymer of Formula (I) is present in a fluid sample at a concentration of 0.1-10,000 nM, preferably 1-5,000 nm, preferably 10-1,000 nM, preferably 15-500 nM, preferably 20-250 nM to form a mixture. An ultraviolet visible absorption profile of the mixture may be measured, wherein the presence of $I^-$ ions is manifested by the appearance of an ultraviolet visible absorption peak at 290-300 nm, preferably 292-298 nm, preferably 294-296 nm, or about 295 nm, and/or an ultraviolet visible absorption peak at 360-370 nm, preferably 362-368 nm, preferably 364-366 nm, or about 365 nm that is substantially not present in the fluid sample prior to the contacting. Thus, the copolymer of Formula (I) described herein can be considered as a "turn-on" chemosensor for iodide anions. In many embodiments, the color difference of the copolymer before and after exposing to iodide anions can be detectable by naked-eye (e.g. a color change from colorless to yellow). The chromatic change may be due to formation of intermolecular charge-transfer complexes between the copolymer and the iodide ions, and/or changes in the aggregation and planarity of the copolymer in the presence of the iodide anions.

There are various parameters in the method under which ions are detected in the fluid sample. Parameters such as contact time, contact temperature, and agitation speed can be varied and their impacts on detection may be noted. In a preferred embodiment, the copolymer is contacted with the fluid sample for 1 second to 24 hours, preferably 1 minute to 18 hours, preferably 5 minutes to 12 hours, preferably 15 minutes to 8 hours, preferably 30 minutes to 6 hours, preferably 45 minutes to 5 hours, preferably 60 minutes to 4 hours, preferably 90 minutes to 3 hours. In a preferred embodiment, the copolymer of the present disclosure is effective in detecting iodide anions in a fluid sample within a temperature range of 10-100° C., preferably 20-80° C., preferably 25-60° C., preferably 25-40° C., preferably 25-30° C., or room temperature. In one embodiment, the method further comprises agitation of the fluid sample before, during, or after the contacting. The agitation can encompass shaking, stirring, rotating, vibrating, sonicating and other means of increasing contact between the copolymer and the iodide ion. Further, agitation can be performed by hand or mechanically. In one embodiment, the contacting and detecting process may be enhanced by mechanical shaking or agitation, preferably by a centrifuge at a speed of up to 800 rpm, preferably 50-600 rpm, preferably 100-500 rpm, preferably 200-400 rpm in order to increase contact between the copolymer and the iodide ions.

In a preferred embodiment, the method described herein has a anion detection lower limit of 0.3-2.6 mM in the presence of one or more additional anions and counter cations, preferably 0.4-2.5 mM, preferably 0.5-2.4 mM, preferably 0.6-2.3 mM in the presence of one or more additional anions and counter cations. In some embodiments, copolymers of Formula (I) wherein each $R_5$ is dodecyl have smaller detection lower limit (higher sensitivity) for than copolymers wherein each $R_5$ is 2-ethylhexyl by 20%-90%, preferably 30%-80%, preferably 40%-70%, preferably 50%-60%. In a preferred embodiment, the one or more additional anions are at least one selected from the group consisting of $Br^-$, $Cl^-$, $F^-$, $NO_3^-$, and $CN^-$. In certain embodiments, these additional anions may be present in up to 1,000,000 equivalents excess to the copolymer of Formula (I) without interfering with the detection of anions, preferably up to 500,000 equivalents, preferably up to 100,000 equivalents, preferably up to 100,000 equivalents, preferably up to 10,000 equivalents excess to the copolymer without interfering with the detection of I anions. In one or more embodiments, the nature of the counter cations present in the fluid sample does not influence the detection of anions using the aforementioned method. In a preferred embodiment, the one or more additional counter cations are at least one selected from the group consisting of $Na^+$, $K^+$, $NH_4^+$, and $N[(CH_2)_3CH_3]_4^+$.

In certain embodiments, the methods described herein selectively detect a presence of anions in a fluid sample which further contains one or more other anions selected from the group consisting of $CH_3COO^-$, $BF_4^-$, $H_2PO_4^-$, $HPO_4^{2-}$, $PO_4^{3-}$, $NO_2^-$, $SCN^-$, $CO_3^{2-}$, $SO_4^{2-}$, and/or one or more other counter cations selected from the group consisting of $Cu^{2+}$, $Mg^{2+}$, $Fe^{2+}$, $Ni^{2+}$, $Ba^{2+}$, $CO^{2+}$, $Zn^{2+}$, $Mn^{2+}$, $Cr^{3+}$, $Cd^{2+}$, $Co^{2+}$, $Ni^{2+}$.

According to another aspect, the present disclosure relates to a membrane comprising (i) a polymer selected from the group consisting of polyvinyl chloride, polystyrene, polyethylene, and poly(methyl methacrylate), and (ii) 0.1 to 75 wt % of the copolymer relative to a total weight of the membrane, wherein the copolymer is dispersed with the polymer.

As used herein, a polymer is introduced to disperse the copolymer in solid state and add physical strength and durability and portability to the copolymer of the present disclosure. Other polymers suitable for the purpose of present disclosure include, but are not limited to, polyvinyl chloride (PVC), polystyrene (PS), polyethylene (PE), and poly(methyl methacrylate) (PMMA). It is equally envisages that the membrane described herein may be adapted to incorporate additional polymers such as polyurethane, polyethylene terephthalate, polyester, polyvinylidene chloride, polypropylene (PP), polyamides, nylons, polysulfones, fluoropolymers (e.g., polyvinylidene fluoride (PVDF), polytetrafluoroethylene (PTFE)), silicones (e.g., polydimethylsiloxane (PDMS) and polymethylphenylsilicone (PMPS)), acrylonitrile butadiene styrene (ABS), polyethylene/acrylonitrile butadiene styrene (PE/ABS), polycarbonate (PC), and polycarbonate/acrylonitrile butadiene styrene (PC/ABS).

In some embodiments, the membrane is prepared by casting a mixture of the aforementioned polymer, the copolymer of the present disclosure, and an optional solvent. A solvent may be optionally used to help dissolve the polymers and copolymers to form a homogeneous membrane solution, thus disperse the copolymer with the polymer. The solvent is chosen primarily for its ability to completely dissolve the polymers and the copolymer and for the ease of solvent removal in the membrane formation steps. Preferred solvents include dichloromethane, chloroform, acetone, tetrahydrofuran, acetonitrile, diethyl ether, ethyl acetate, pentane, hexanes, dioxanes, methanol, ethanol, and mixtures thereof. A total amount of polymer and the copolymer of the present disclosure may be in a range of 5-50 wt %, 10-40 wt %, or 20-30 wt % relative to a weight of the membrane solution.

To produce a membrane, the membrane solution may be cast by a continuous single extrusion film process, flow casting, spin casting, or solvent casting. In one embodiment, the membrane solution may be cast onto a glass slide and a casting knife may be used for spreading the membrane solution across the glass slide to a uniform membrane thickness. After evaporation of the solvent, the membrane may be peeled off from the glass slide. In a preferred embodiment, the copolymer is present in an amount of 0.1 to 75 wt % relative to a total weight of the membrane, preferably 1-70 wt %, preferably 5-65 wt %, preferably 10-60 wt %, preferably 20-50 wt %, preferably 30-40 wt % relative to a total weight of the membrane.

In another embodiment, the membrane described herein is further supported by a substrate. The substrate can be made of any material that is wettable by the membrane solution and inert to the components in the membrane solution, stable under fabrication process, and one to which the membrane thus formed will adhere. Non-limiting examples of substrates include crystalline substrates such as silica based substrates (e.g. glass, quartz, silicon, silica aerogels, or the like), substrates for semiconductor and microprocessor applications (e.g. gallium arsenide, indium-doped gallium nitride), paper, and polymers. A dip coating method may be used. After application of the membrane solution to the substrate, a heating or calcination step may be carried out. Dip coating steps may be repeated several times (e.g. 1-50 times, 5-30 times, or 10-20 times) to form a desired thickness of membrane coating.

In some embodiments, the membrane is a thin film membrane and has a thickness of about 100-1,000 µm, about 200-800 µm, about 300-700 µm, or about 400-600 µm. In certain embodiments where the membrane is disc-shaped, a diameter of the membrane may be 1-100 mm, 5-80 mm, or 10-50 mm. In some embodiments, the membrane is in a form of a rectangular sheet having a width of 2-200 mm, 8-150 mm, or 15-70 mm.

The membrane described herein may be used as a portable sensor in detecting iodide anions in a fluid sample or in a solid sample collected from aforementioned sources. In one embodiment, a color change of the membrane occurs upon contacting the membrane with iodide anions, which may be measurable by a UV-vis spectrometer (e.g. an appearance of an ultraviolet visible absorption peak at around 360 nm) and/or detected by naked-eye. Additionally, the membrane may have utility as an organic semiconductor in optical devices, more typically used as organic field effect transistors (OFET) in electronic applications, fuel cell electrodes, liquid crystal display (LCD), organic light emitting diodes (OLEDs), and organic photovoltaic (OPV).

The examples below are intended to further illustrate protocols for preparing and characterizing the copolymers of the present disclosure. Further, they are intended to illustrate iodide sensing properties of these copolymers. They are not intended to limit the scope of the claims.

EXAMPLE 1

Synthesis of 4,4'-(3-hexylthiophene-2,5-diyl)dibenzaldehyde (12)

Deionized water (3 mL) was added to a mixture of boronic ester 11 (0.58 g, 2.5 mmol), dibromo-3-hexylthiophene (0.33 g, 1.0 mmol), t-butylammonium bromide (0.64 g, 2.0 mmol) and sodium carbonate (0.40 g, 3.8 mmol) in a microwave (MW) vessel under nitrogen atmosphere. After bubbling nitrogen through the mixture for 3 minutes, [$PdCl_2$(dppf)] (0.08 g, 0.1 mmole) was added to the reaction mixture and the vessel was then placed inside a CEM Discover S-Class microwave synthesizer. The reaction was exposed to microwaves at 80° C. (100 W) for 15 minutes and then diluted with ethyl acetate (20 mL) at room temperature followed by filtration through a pad of celite. The organic layer was washed with brine (5 mL), dried over $Na_2SO_4$ and evaporated under reduced pressure. The residues were resolved over silica column, eluting with ethyl acetate-hexane (15:85) to get the title compound 12 as a light yellow solid (0.35 g, 86%). $^1$H-NMR (500 MHz, $CDCl_3$): δ 0.89 (t, J=7.0 Hz, 3H, $CH_3$), 1.29-138 (m, 8 H, Aliphatic-H), 1.69 (m, 2H, Aliphatic-H), 2.73 (t, J=6.7 Hz, 2H, $CH_2$), 7.41 (s, 1H, Ar—H), 7.66 (d, J=7.6 Hz, 2H, Ar—H), 7.78 (d, J=7.5 Hz, 2H, Ar—H), 7.92 (d, J=8.2 Hz, 2H, Ar—H), 7.97 (d, J=8.1 Hz, 2H, Ar—H), 10.03 (s, 1H, CHO), 10.08 (s, 1H, CHO).

EXAMPLE 2

Synthesis of P1 t-BuONa (0.40 g, 4.16 mmol) was added to a solution of dialdehyde 12 (0.31 g, 0.83 mmol) and diphosphonate 6 (0.62 g, 0.83 mmol) in anhydrous DMF (30 mL) under nitrogen atmosphere and the mixture was stirred for 24 h at 100° C. After cooling to the room temperature, the mixture was poured over 200 mL of methanol and the product was centrifuged. The solvent was decanted and the residue was re-dissolved in a minimum amount of THF and successively re-precipitated from methanol, isopropanol, and hexane to get the final product as a dark yellow solid (0.25 g, 80%). $^1$H-NMR (500 MHz, $CDCl_3$): δ 0.86 (br., 9H), 1.23-1.42 (m, 48H), 1.67 (m, 2H), 2.80 (br. m, 2H), 4.03 (br. m, 4H), 7.05-7.13 (br., 4H), 7.44-7.79 (br., 11H).

EXAMPLE 3

Synthesis of P2

Following the same protocol adopted for the synthesis of P1, P2 was obtained from the reaction of monomers 7 and 12 as a light yellow solid (0.25 g, 85%). $^1$H-NMR (500 MHz, $CDCl_3$): δ 0.89 (br. m, 12H), 1.31-1.67 (m, 29H), 1.89 (m, 2H), 2.77 (br. m, 2H), 4.04 (br. m, 4H), 7.03-7.18 (br., 4H), 7.44-7.82 (br., 11H).

EXAMPLE 4

Synthesis of P3

Diacetonitrile 8 (0.28 g, 0.53 mmol) was added to a solution of dialdehyde 12 (0.20 g, 0.53 mmol) in a mixture of THF (17 mL) and t-BuOH (17 mL), which was followed by the addition of t-BuONa (0.25 g, 1.59 mmol) at room temperature. The mixture was then heated for 12 hours at 70° C. After cooling to the room temperature, the mixture was poured over ice cold methanol and acidified with acetic acid (1 mL). The resultant precipitates were filtered and precipitated from methanol to get the title copolymer P3 as a dark red amorphous solid (0.20 g, 70%). $^1$H-NMR (500 MHz, CDCl$_3$): δ 0.86 (br. m, 9H), 1.23-1.42 (m, 48H), 1.67 (br. m, 2H), 2.74 (br. m, 2H), 4.06 (br. m, 4H), 7.15 (br. m, 2H), 7.22-7.42 (br. m, 8H), 7.83 (br., 1H) 8.21 (br., 2H).

EXAMPLE 5

Synthesis of P4

Following the same protocol adopted for the synthesis of P3, P4 was obtained from the reaction of monomers 9 and 12 as a dark red amorphous solid (Yield: 0.195 g, 74%). $^1$H-NMR (500 MHz, CDCl$_3$): δ 0.92 (br. m, 12H), 1.26-1.60 (br. m, 29H), 1.77 (br., 2H), 2.74 (br. m, 2H), 3.85 (br. m, 4H), 7.10 (br. m, 2H), 7.21-7.46 (br. m, 8H), 7.89 (br., 1H) 8.25 (br., 2H).

EXAMPLE 6

Description of Synthetic and Characterizing Methods

The synthesis of monomers 6-9 were achieved as outlined in FIG. 1. In short, the O-alkylation of hydroquinone 1 with dodecyl bromide or 3-(bromomethyl)heptane [Aggarwal, A. V.; Jester, S. S.; Taheri, S. M.; Førster, S.; Höger, S. *Chemistry* 2013, 19, 4480; and Zhu, X.; Traub, M. C.; Bout, D. A. V.; Plunket, K. N. *Macromolecules* 2012, 45, 5051, each incorporated herein by reference in their entirety] followed by the bromomethylation with paraformaldehyde and sodium bromide in a mixture of acetic acid and sulfuric acid furnished the dibromides 4 and 5. Condensation of 4 and 5 with triethyl phosphite in refluxing toluene rendered diphosphonates 6 and 7, respectively. The reaction of 4 and 5 with sodium cyanide in DMF produced dinitrile monomers 8 and 9, respectively (FIG. 1).

Figure 2:
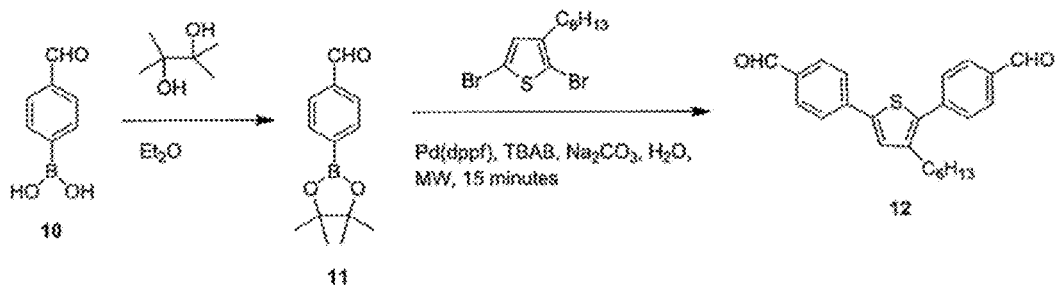
FIG. 2 is a synthetic scheme for a dialdehyde of Formula (VI), wherein each $R_1$ and $R_2$ are a hydrogen, and $R_3$ is n-hexyl (compound 12).

Likewise, the boronic acid 10 was transformed to the known boronic ester 11 [Oehlke, A.; Auer, A. A.; Jahre, I.; Walfort, B.; Rüffer, T.; Zoufala, P.; Lang, H.; Spange, S. *J. Org. Chem.* 2007, 72, 4328, incorporated herein by reference in its entirety], which in turned was reacted with 2,5-Dibromo-3-hexylthiophene (DBHT) under Suzuki-Miyaura condition in a microwave reactor to produce the dialdehyde monomer 12 in high yield. It is worth mentioning that the synthesis of 12 was also attempted by reacting boronic acid 10 with DBHT under Suzuki-Miyaura conditions, using Pd(PPh$_3$)$_4$ or [1,1'-bis(diphenylphosphino)-ferrocene]dichloropalladium(II) as catalysts but these trials led to the formation of the desired 12 in a moderate yield (57%) coupled with the formation of fewer side products. Likewise, the reaction of 11 with DBHT in a microwave reactor in the presence of t-butylammonium bromide (TBAB) and Na$_2$CO$_3$ in water did not produce any desired product (FIG. 2) [Leadbeater, N. E.; Marco, M. *J. Org. Chem.* 2003, 68, 5660, incorporated herein by reference in its entirety].

Figure 3:
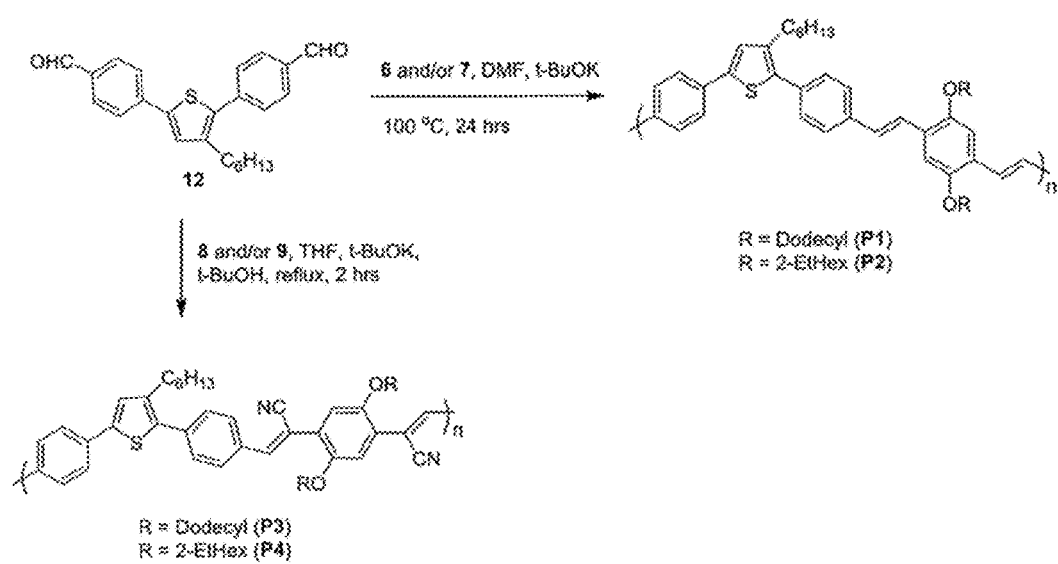
FIG. 3 is a synthetic scheme for a copolymer of Formula (II) (P2), a copolymer of Formula (III) (P3), a copolymer of Formula (IV) (P1), a copolymer of Formula (V) (P4).
Figure 4A:
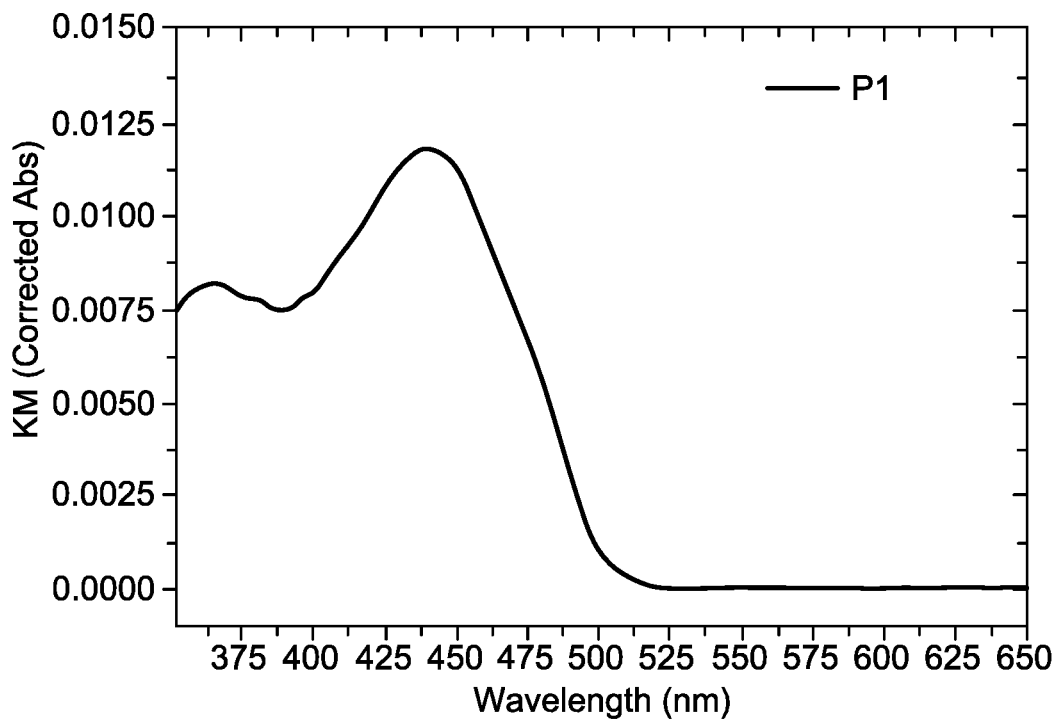
FIG. 4A is an ultraviolet-visible (UV-vis) absorption spectrum of a copolymer of Formula (IV) (P1) in thin film state.
Figure 4B:
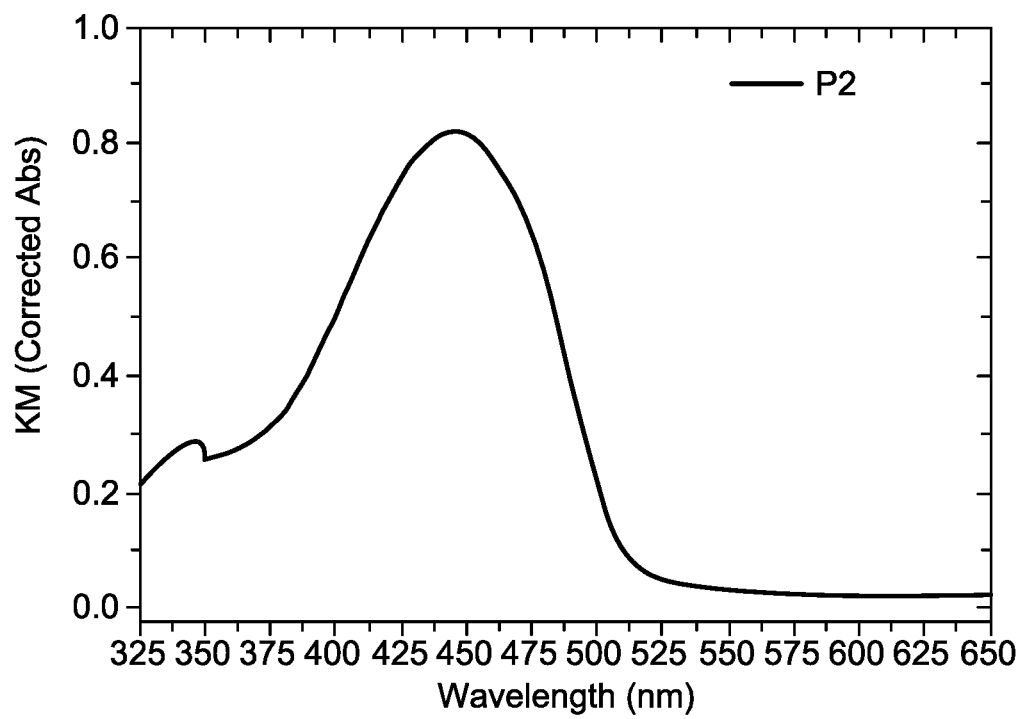
FIG. 4B is a UV-vis absorption spectrum of a copolymer of Formula (II) (P2) in thin film state.
Figure 4C:
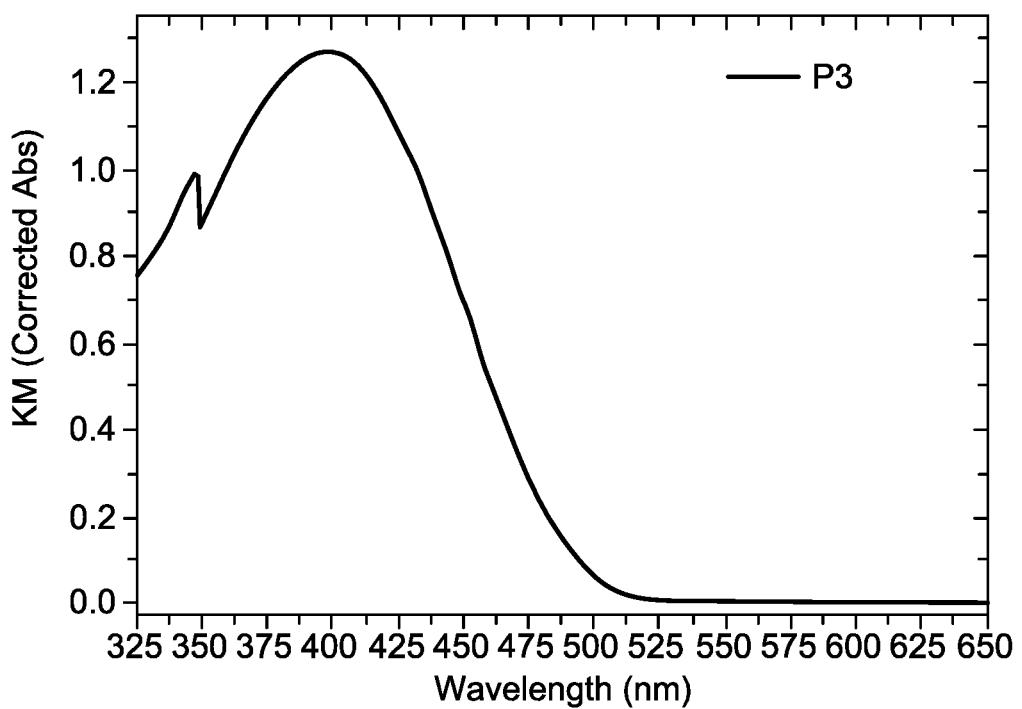
FIG. 4C is a UV-vis absorption spectrum of a copolymer of Formula (III) (P3) in thin film state.
Figure 4D:
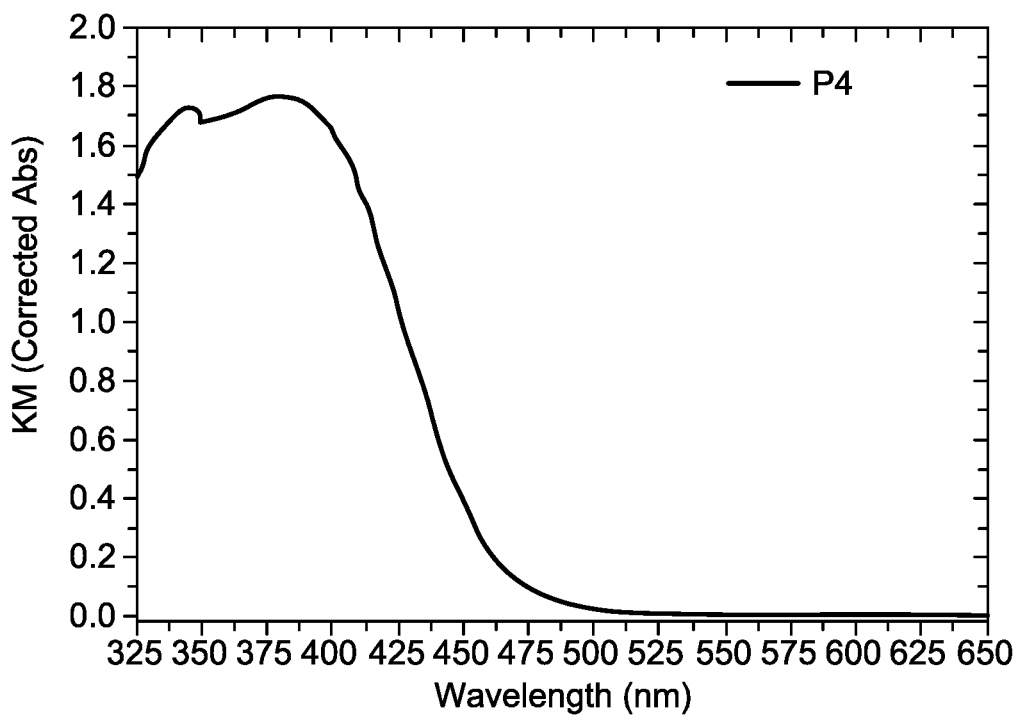
FIG. 4D is a UV-vis absorption spectrum of a copolymer of Formula (V) (P4) in thin film state.

To maximize the stereoregularity and regioregularity of newly formed vinylene groups, the copolymers P1 and P2 were synthesized via Horner-Emmons reaction with excellent E olefin stereochemistry. The Horner-Emmons polymerization was carried out by slow addition of 5 equiv of base, t-BuONa, to the solution of monomers 12 and 6 or 7 in DMF and was then stirred for 24 hours at 100° C. After quenching the polymerization with aqueous ammonium chloride, the mixture was poured into excess methanol, centrifuged and re-precipitated in methanol, isopropanol, and hexane successively to render P1 and P2 in good yield (80%) (FIG. 3).

The polymerization of P3 and P4 were accomplished by Knoevenagel condensation [Sotzing, G. A.; Thomas, C. A.; Reynolds, J. R.; Steel, P. J. *Macromolecules* 1998, 31, 3750, incorporated herein by reference in its entirety] between the aromatic acetonitriles 8 or 9 with dialdehyde 12 in a 1:1 mixture of t-BuOH/THF with 1.5 equiv of t-BuONa per cyano group of monomers 8 or 9 (Scheme 3). After stirring for 12 h at 70° C., reaction mixture was cooled to room temperature and poured to ice cold methanol, which was followed by acidification with acetic acid. The precipitated polymer was dissolved in chloroform and re-precipitated in methanol to obtain the desired polymers P3 and P4 as red colour amorphous solids. All the synthesized polymers are soluble in common organic solvents such as chloroform, methylene chloride and tetrahydrofuran. The $^1$H-NMR and IR spectra supported the structures of the synthesized polymers. For instance, end groups of phosphonate monomers of 6 and 7 were not visible in the $^1$H-NMR of P1 and P2. Similarly, characteristic aldehyde peaks of 12 at 2850, 2730 and 1700 cm$^{-1}$ disappeared in P1-P4. In addition, residual nitrile IR stretching bands at ~2250 cm$^{-1}$ corresponding to the monomers 8 and 9 shifted to ~2210 cm$^{-1}$ in P3 and P4, indicating the presence of conjugated cyanovinylene linkages. Molecular weight analyses of P1-P4 were performed by GPC (polystyrene standards, THF as mobile phase) and the molecular weights and polydispersity indexes are summarized in Table 1.

TABLE 1

Summary of molecular weight and polydispersity index of P1-P4

| Polymer | Mp | Mn | Mw | Mz | PDI |
|---|---|---|---|---|---|
| P1 | 7785 | 7363 | 13509 | 23180 | 1.83 |
| P2 | 21074 | 14097 | 25287 | 41163 | 1.79 |
| P3 | 3417 | 3012 | 5639 | 10421 | 1.87 |
| P4 | 5411 | 4221 | 10155 | 23376 | 2.41 |

Mp = peak molecular weight;
Mn = number-average molecular weight;
Mw = weight-average molecular weight;
Mz = Z-average molecular weight; and
PDI = polydispersity index.

EXAMPLE 7

Photophysical Properties

UV-vis absorption and fluorescence emission spectroscopic techniques were used to evaluate the optical properties of the polymers. The baseline-corrected UV-vis (KM) absorption spectra of synthesized polymers in thin film state were prepared by dropping 250 μL solution of copolymer dissolved in THF (2.5 mg/mL) on the surface of indium tin oxide (ITO), as shown in FIGS. 4A-4D. Broad absorption bands near 440, 445, 398 and 380 nm were observed for P1-P4, respectively. Unsymmetrical branching on the phenylene ring of P4 results in a shift of absorption to the blue region by 18 nm compared to P3, which was attributed due to the steric hindrance imparted on the cyanovinylenes polymer disorder and conjugation. However, branching on the phenylene ring of vinylenes (P1 and P2) seems to have no significant influence [Colladet, K.; Fourier, S.; Cleij, T. J.; Lutsen, L.; Gelan, J.; Vanderzande, D. *Macromolecules* 2007, 40, 65, incorporated herein by reference in its entirety]. Although the polymers are amorphous in nature, one can clearly observe the strong shoulder peaks in the UV-vis spectra of these polymers, suggesting good π-π stacking between polymer chains (FIGS. 4A-4D) [Choi, T.-L.; Han, K.-M.; Park, J.-II.; Kim, D. H.; Park, J.-M.; Lee, S. *Macromolecules* 2010, 43, 6045, incorporated herein by reference in its entirety].

Figure 5:
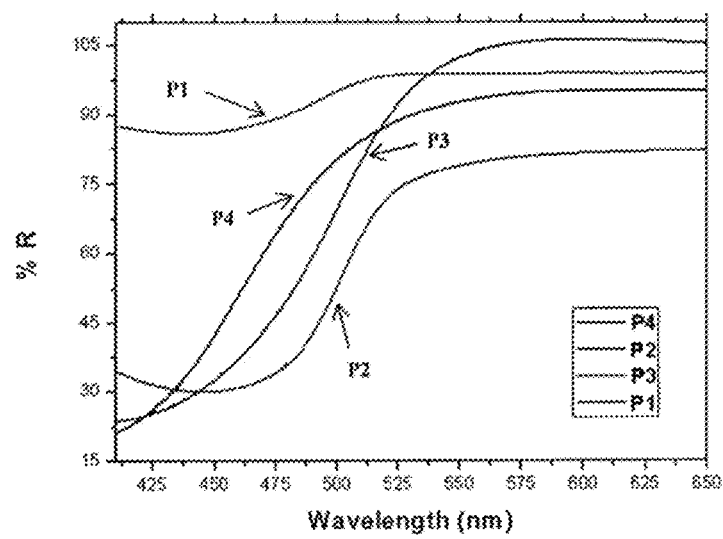
FIG. 5 is an overlay of UV-vis reflectance spectra of copolymers of Formula (IV) (P1), Formula (II) (P2), Formula (III) (P3), and Formula (V) (P4) in thin film state.

The optical band gaps of all the polymers were determined by the onset of UV-vis absorption spectra. The onset absorptions of P1-P4 films, as shown in Table 2, were ranging between 515-530 nm, corresponding to optical band gaps of 2.34-2.41 eV. Moreover, the onset absorption edges of polymers films (FIG. 5) were found to be between 530-575 nm, which were corresponded to band gaps of 2.15-2.34 eV (Table 2).

TABLE 2

Comparison of bandgap measurements by DR UV-vis

| Polymers | $\lambda_{max}$ | KM Vs nm On set Wavelength | Band Gap | % R Vs nm Absorption edge Wavelength | Band Gap |
|---|---|---|---|---|---|
| P1 | 440 nm | 516 nm | 2.40 eV | 530 nm | 2.34 eV |
| P2 | 445 nm | 530 nm | 2.34 eV | 565 nm | 2.19 eV |
| P3 | 398 nm | 525 nm | 2.36 eV | 570 nm | 2.18 eV |
| P4 | 380 nm | 515 nm | 2.41 eV | 575 nm | 2.15 eV |

Figure 6:
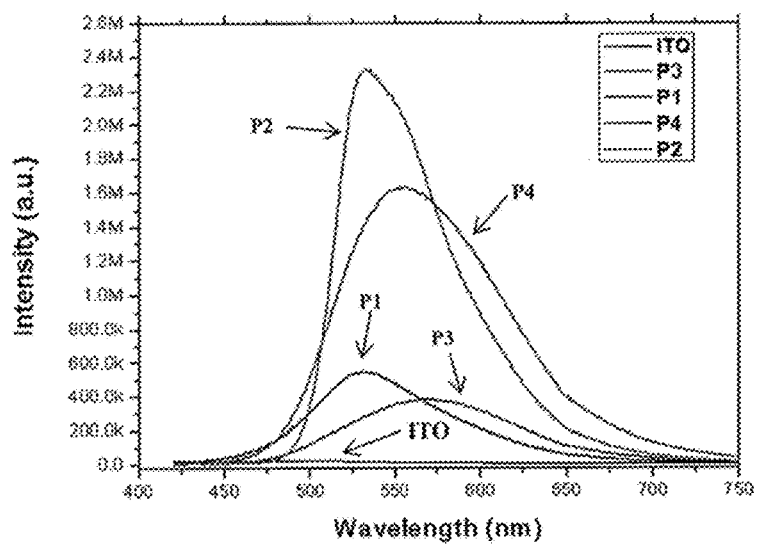
FIG. 6 is an overlay of fluorescence emission spectra of copolymers of Formula (IV) (P1), Formula (II) (P2), Formula (III) (P3), and Formula (V) (P4) in thin film state upon excitation at 390 nm.

The relatively low band gaps of P3 and P4 can be attributed to the greater intramolecular charge transfer (ICT) between electron donor segments such as thiophene and/or dialkoxybenzene and strong electron acceptor segment like cyanovinylene spacer [Ortiz, R. P.; Yan, H.; Facchetti, A.; Marks. T. J. *Materials* 2010, 3, 1533; and Lee, W.-Y.; Cheng, K.-F.; Liu, C.-L.; Lin, S.-T.; Chueh, C.-C.; Tsai, F.-Y.; Chen, W.-C. *J. Polym. Res.* 2009, 16, 239, each incorporated herein by reference in their entirety]. Fluorescence emission spectra of the polymers in thin film state were recorded with the excitation wavelength of 390 nm. Whereas a lower intensity emission maxima for P1 and P3 were observed at 530 and 577 nm, respectively, higher intensity emission maxima for P2 and P4 appeared at 533 and 550 nm. In addition, cyanovinylenes P3 and P4 have shown a bathochromic shift of 37 and 17 nm, respectively, compared to their vinylene counterparts P1 and P2 (FIG. 6).

EXAMPLE 8

Thermal Properties

Figure 7:
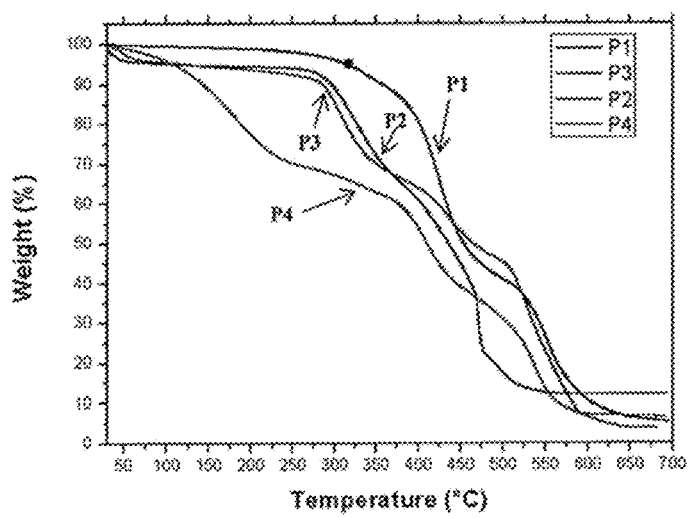
FIG. 7 is an overlay of thermogravimetric analysis (TGA) of copolymers of Formula (IV) (P1), Formula (II) (P2), Formula (III) (P3), and Formula (V) (P4).

The thermal properties of synthesized polymers were evaluated by thermogravimetric analysis (TGA) under oxygen atmosphere at a heating rate of 10° C. min$^{-1}$. Polymers P1-P3 were found to be stable even at high temperatures up to 300° C. with no appreciable loss of mass (FIG. 7). As shown in FIG. 7, the onset decomposition temperatures ($T_d$) of P1-P3 were at 285, 280 and 300° C., respectively. As the temperature increased above $T_d$, the weight loss increased abruptly, indicating the decomposition of the polymer backbone. However, the onset decomposition temperature of P4 was 115° C. and weight loss increased with increasing temperature.

EXAMPLE 9

Electrochemical Properties

Figure 8A:
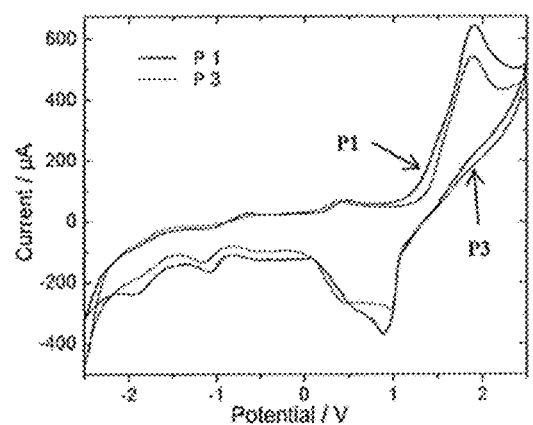
FIG. 8A is an overlay of cyclic voltammograms of copolymers of Formula (IV) (P1), and Formula (III) (P3).
Figure 8B:
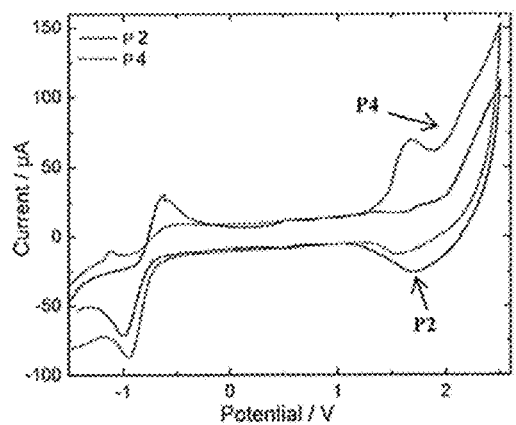
FIG. 8B is an overlay of cyclic voltammograms of copolymers of Formula (II) (P2), and Formula (V) (P4).
Figure 9A:
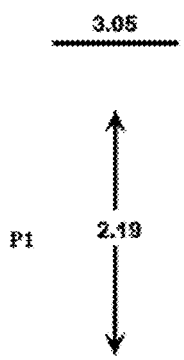
FIG. 9A depicts the electrochemical band gap energy diagram of a copolymer of Formula (IV) (P1).
Figure 9B:
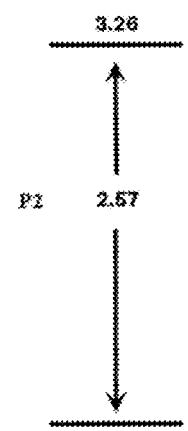
FIG. 9B depicts the electrochemical band gap energy diagram of a copolymer of Formula (II) (P2).
Figure 9C:
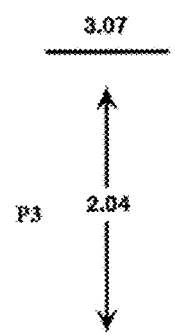
FIG. 9C depicts the electrochemical band gap energy diagram of a copolymer of Formula (III) (P3).
Figure 9D:
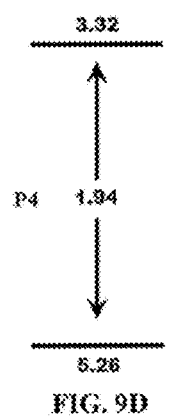
FIG. 9D depicts the electrochemical band gap energy diagram of a copolymer of Formula (V) (P4).
Figure 10A:
FIG. 10A shows color change observed 0 min and 12 hours after addition of different salts including Br⁻ (NaBr, TBABr (tetrabutylammonium bromide)), Cl⁻ (NaCl), F⁻ (NaF), I⁻ (TBAI (tetrabutylammonium iodide), NaI, and KI), $NO_3^-$ ($NH_4NO_3$) and CN⁻ (NaCN) to copolymer of Formula (IV) (P1). Concentrations of P1 and each salt are 0.0287 μM and 12.5 mM, respectively.
Figure 10B:
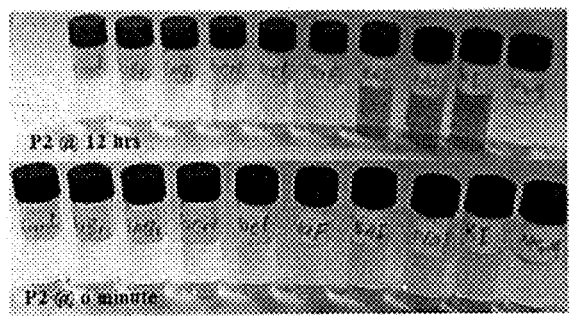
FIG. 10B shows color change observed 0 min and 12 hours after addition of different salts including Br⁻ (NaBr, and TBABr), Cl⁻ (NaCl), F⁻ (NaF), I⁻ (TBAI, NaI, and KI), $NO_3^-$ ($NH_4NO_3$) and CN⁻ (NaCN) to copolymer of Formula (II) (P2). Concentrations of P2 and each salt are 0.0287 μM and 12.5 mM, respectively.
Figure 10C:
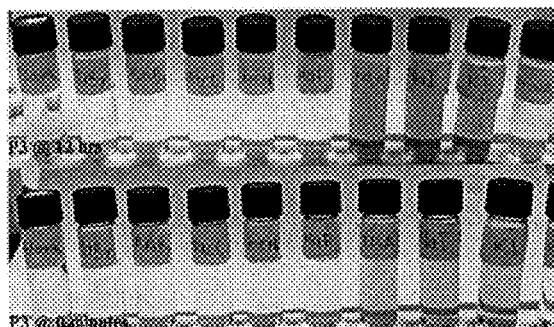
FIG. 10C shows color change observed 0 min and 12 hours after addition of different salts including Br⁻ (NaBr, and TBABr), Cl⁻ (NaCl), F⁻ (NaF), I⁻ (TBAI, NaI, and KI), $NO_3^-$ ($NH_4NO_3$) and CN⁻ (NaCN) to copolymer of Formula (III) (P3). Concentrations of P3 and each salt are 0.0287 μM and 12.5 mM, respectively.
Figure 10D:
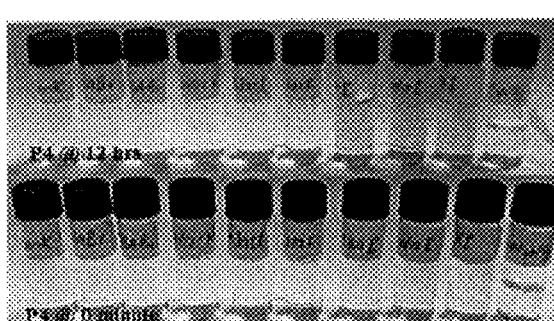
FIG. 10D shows color change observed 0 min and 12 hours after addition of different salts including Br⁻ (NaBr, and TBABr), Cl⁻ (NaCl), F⁻ (NaF), I⁻ (TBAI, NaI, and KI), $NO_3^-$ ($NH_4NO_3$) and CN⁻ (NaCN) salt to copolymer of Formula (V) (P4). Concentrations of P4 and each salt are 0.0287 μM and 12.5 mM, respectively.
Figure 11:
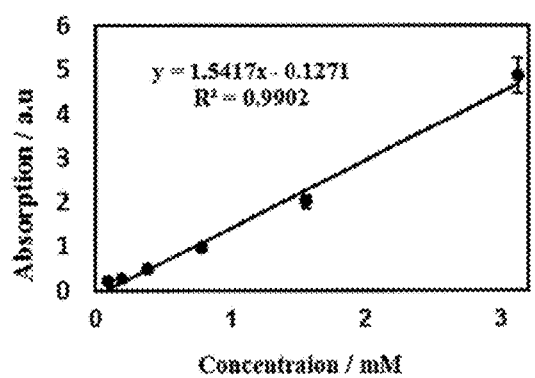
FIG. 11 is a standard calibration curve that plots various concentrations of iodide ion against UV-vis absorption intensities of copolymer of Formula (III) (P3).
Figure 12A:
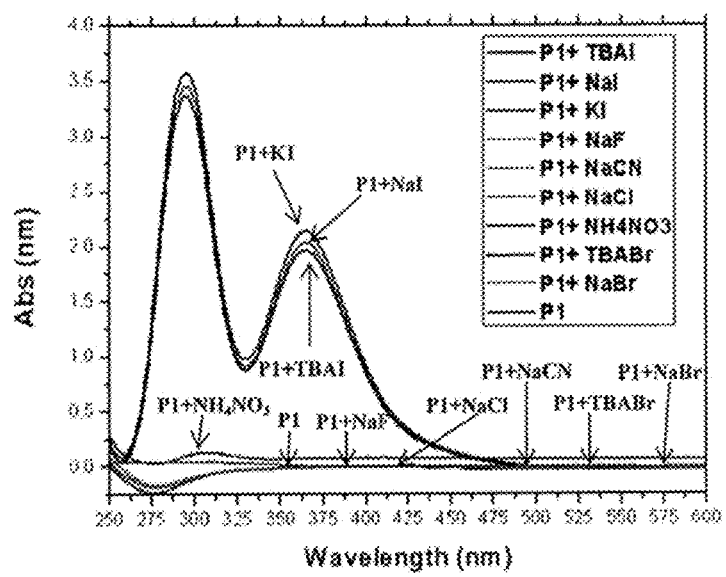
FIG. 12A is an overlay of UV-vis absorption spectra collected 12 hours after addition of different salts including Br⁻ (NaBr, and TBABr), Cl⁻ (NaCl), F⁻ (NaF), I⁻ (TBAI, NaI, and KI), $NO_3^-$ ($NH_4NO_3$) and CN⁻ (NaCN) to copolymer of Formula (IV) (P1). Concentrations of P1 and each salt are 0.0287 μM and 12.5 mM, respectively.
Figure 12B:
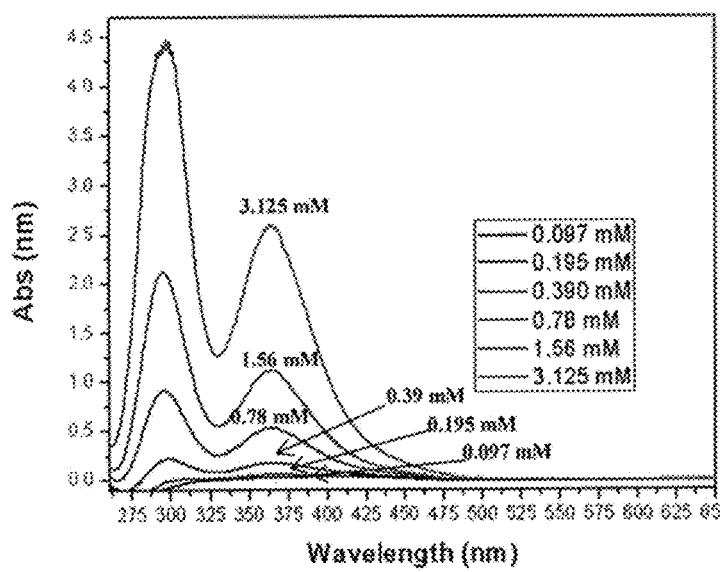
FIG. 12B is an overlay of UV-vis absorption spectra of copolymer of Formula (IV) (P1) at a concentration of 0.0287 μM upon addition of TBAI at different concentrations.
Figure 12C:
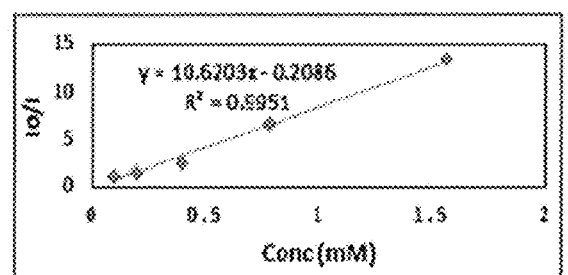
FIG. 12C is a standard calibration curve that plots various concentrations of TBAI against UV-vis absorption intensities of copolymer of Formula (IV) (P1) at a concentration of 0.0287 μM.
Figure 12D:
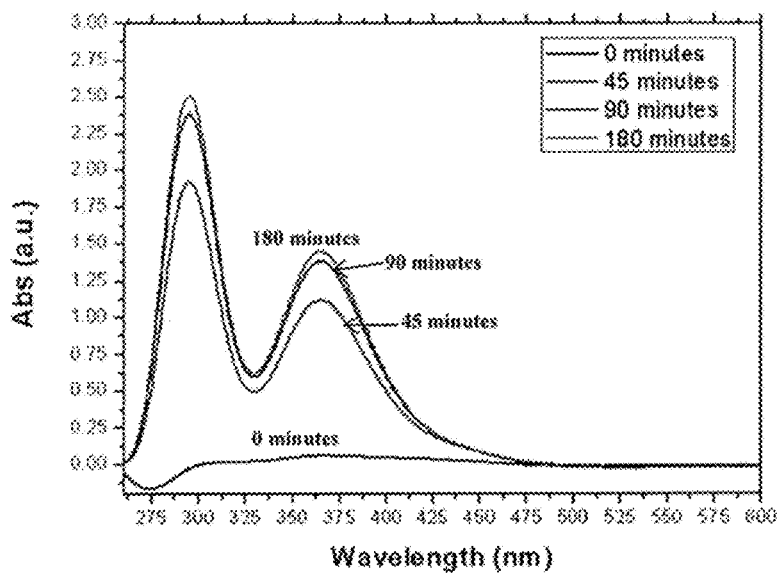
FIG. 12D is an overlay of UV-vis absorption spectra collected at 0 min, 45 min, 90 min, and 180 min after addition of TBAI at a concentration of 0.195 mM to copolymer of Formula (IV) (P1) at a concentration of 0.0287 μM.
Figure 13A:
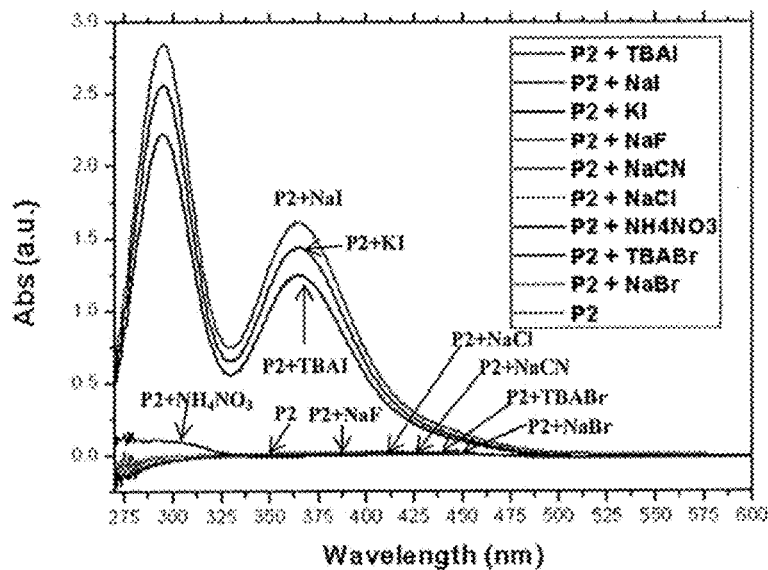
FIG. 13A is an overlay of UV-vis absorption spectra collected 12 hours after addition of different salts including Br⁻ (NaBr, and TBABr), Cl⁻ (NaCl), F⁻ (NaF), I⁻ (TBAI, NaI, and KI), $NO_3^-$ ($NH_4NO_3$) and CN⁻ (NaCN) to copolymer of Formula (II) (P2). Concentrations of P2 and each salt are 0.0287 μM and 12.5 mM, respectively.
Figure 13B:
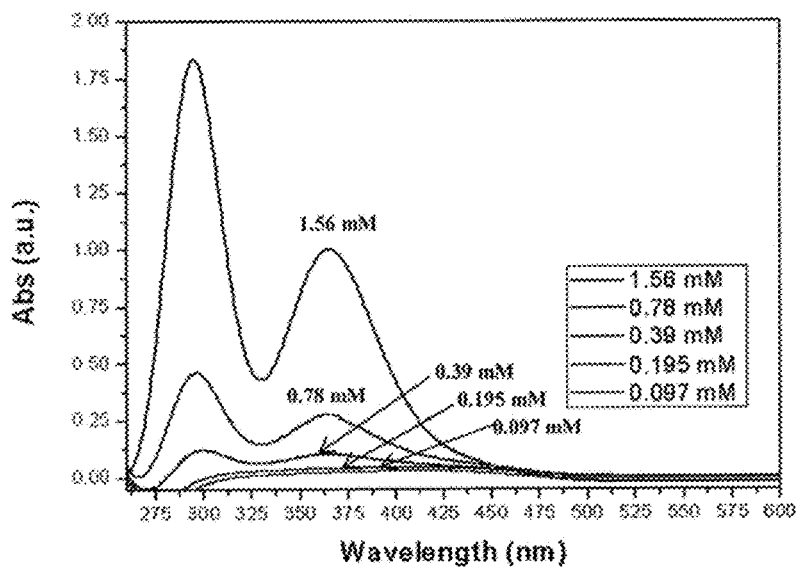
FIG. 13B is an overlay of UV-vis absorption spectra of copolymer of Formula (II) (P2) at a concentration of 0.0287 μM upon addition of TBAI at different concentrations.
Figure 13C:
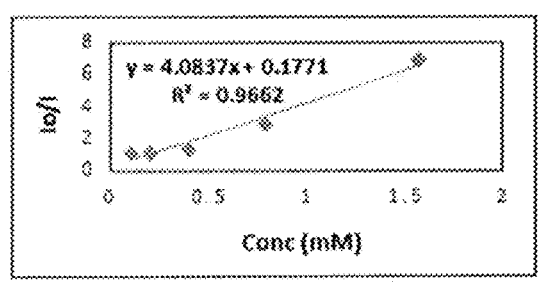
FIG. 13C is a standard calibration curve that plots various concentrations of TBAI against UV-vis absorption intensities of copolymer of Formula (II) (P2) at a concentration of 0.0287 μM.
Figure 13D:
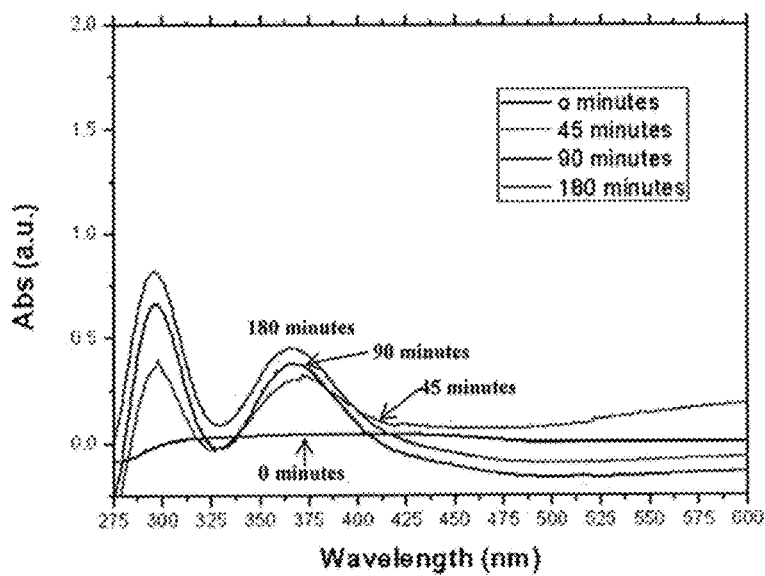
FIG. 13D is an overlay of UV-vis absorption spectra collected at 0 min, 45 min, 90 min, and 180 min after addition of TBAI at a concentration of 0.195 mM to copolymer of Formula (II) (P2) at a concentration of 0.0287 μM.
Figure 14A:
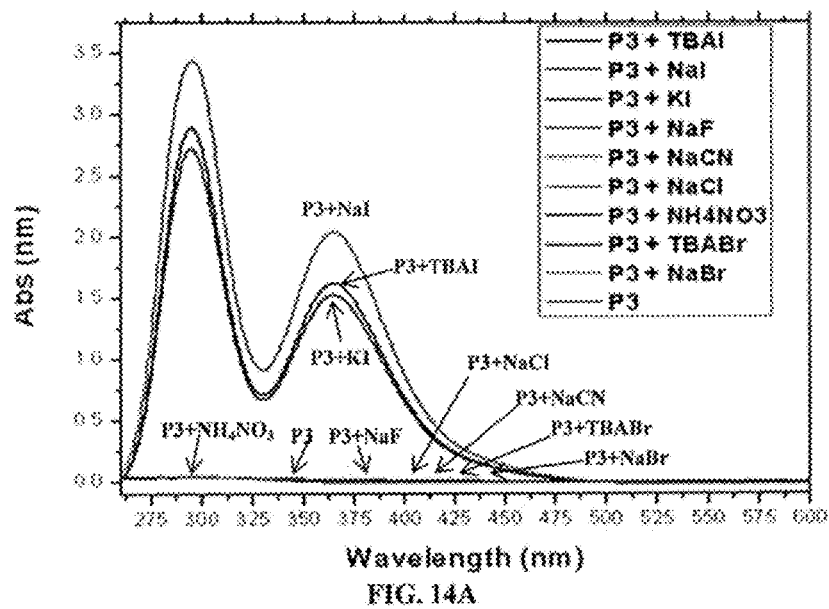
FIG. 14A is an overlay of UV-vis absorption spectra collected 12 hours after addition of different salts including Br⁻ (NaBr, and TBABr), Cl⁻ (NaCl), F⁻ (NaF), I⁻ (TBAI, NaI, and KI), $NO_3^-$ ($NH_4NO_3$) and CN⁻ (NaCN) to copolymer of Formula (III) (P3). Concentrations of P3 and each salt are 0.0287 μM and 12.5 mM, respectively.
Figure 14B:
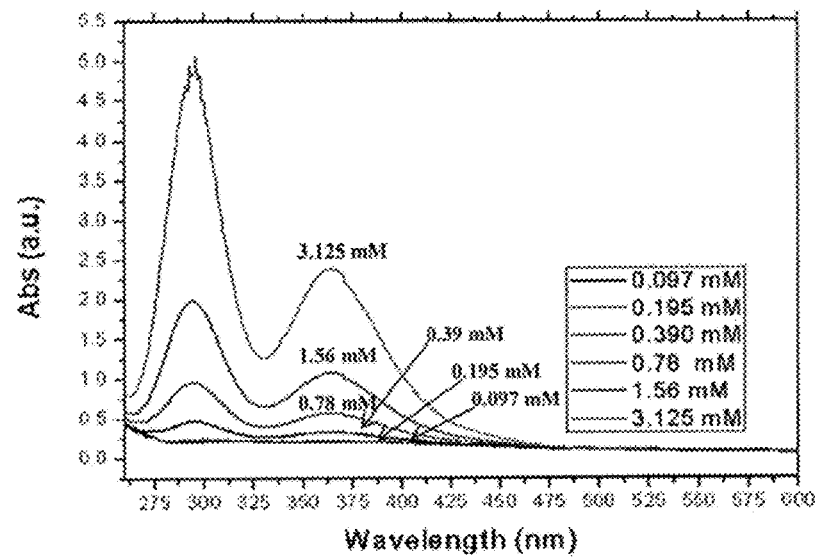
FIG. 14B is an overlay of UV-vis absorption spectra of copolymer of Formula (III) (P3) at a concentration of 0.0287 μM upon addition of TBAI at different concentrations.
Figure 14C:
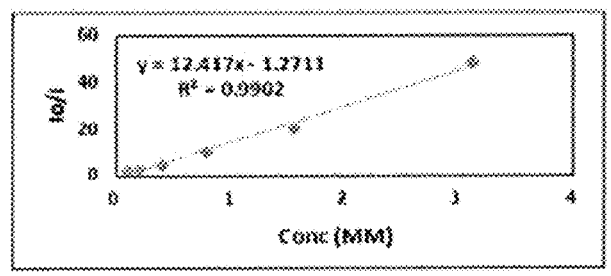
FIG. 14C is a standard calibration curve that plots various concentrations of TBAI against UV-vis absorption intensities of copolymer of Formula (III) (P3) at a concentration of 0.0287 μM.
Figure 14D:
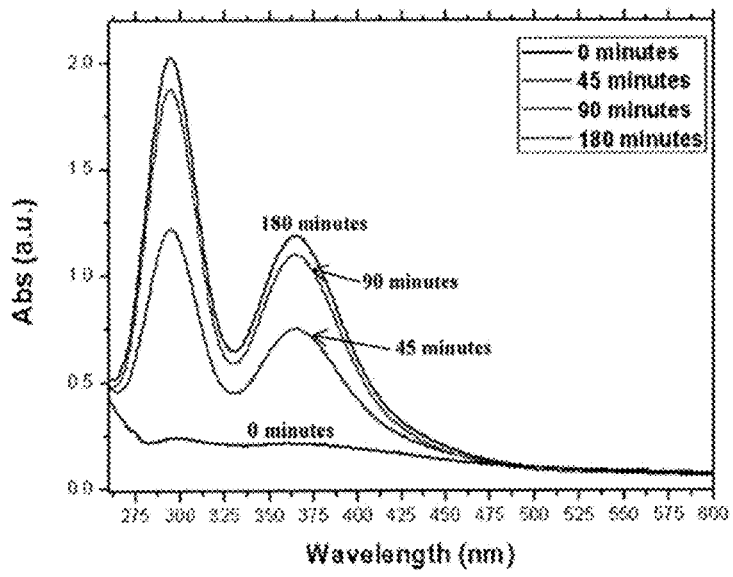
FIG. 14D is an overlay of UV-vis absorption spectra collected at 0 min, 45 min, 90 min, and 180 min after addition of TBAI at a concentration of 0.195 mM to copolymer of Formula (III) (P3) at a concentration of 0.0287 μM.
Figure 15A:
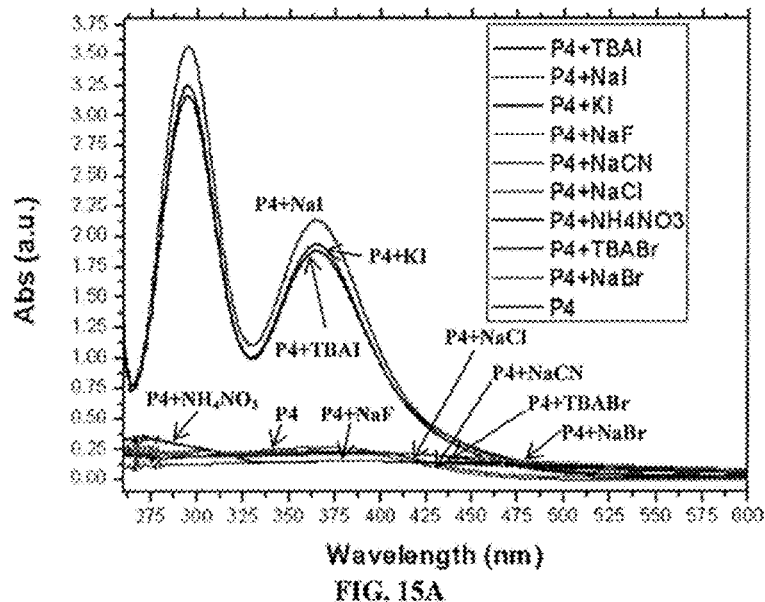
FIG. 15A is an overlay of UV-vis absorption spectra collected 12 hours after addition of different salts including Br⁻ (NaBr, and TBABr), Cl⁻ (NaCl), F⁻ (NaF), I⁻ (TBAI, NaI, and KI), $NO_3^-$ ($NH_4NO_3$) and CN⁻ (NaCN) to copolymer of Formula (V) (P4). Concentrations of P4 and each salt are 0.0287 μM and 12.5 mM, respectively.
Figure 15B:
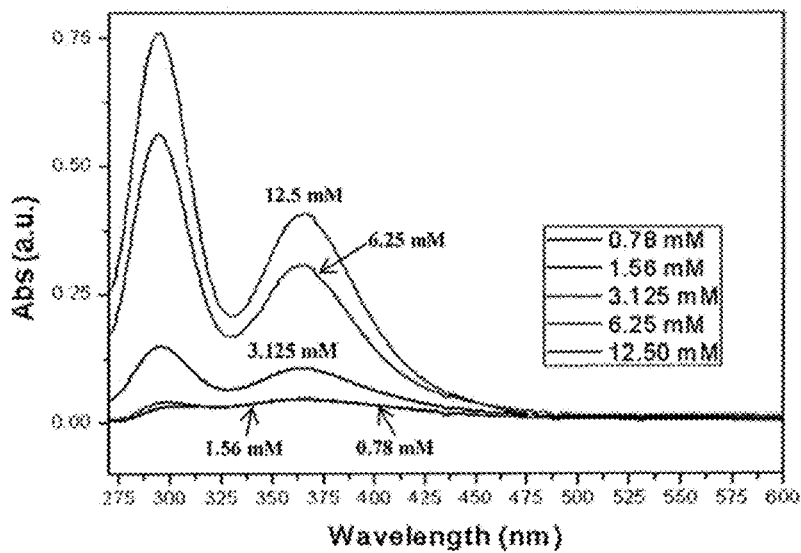
FIG. 15B is an overlay of UV-vis absorption spectra of copolymer of Formula (V) (P4) at a concentration of 0.0287 μM upon addition of TBAI at different concentrations.
Figure 15C:
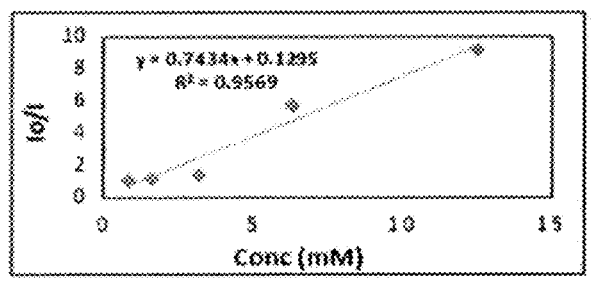
FIG. 15C is a standard calibration curve that plots various concentrations of TBAI against UV-vis absorption intensities of copolymer of Formula (V) (P4) at a concentration of 0.0287 μM.
Figure 15D:
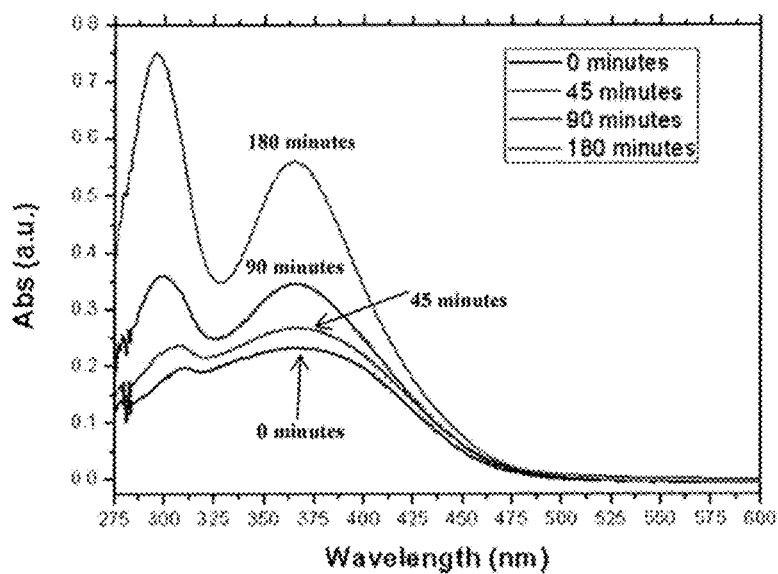
FIG. 15D is an overlay of UV-vis absorption spectra collected at 0 min, 45 min, 90 min, and 180 min after addition of TBAI at a concentration of 0.195 mM to copolymer of Formula (V) (P4) at a concentration of 0.0287 μM.
Figure 16A:
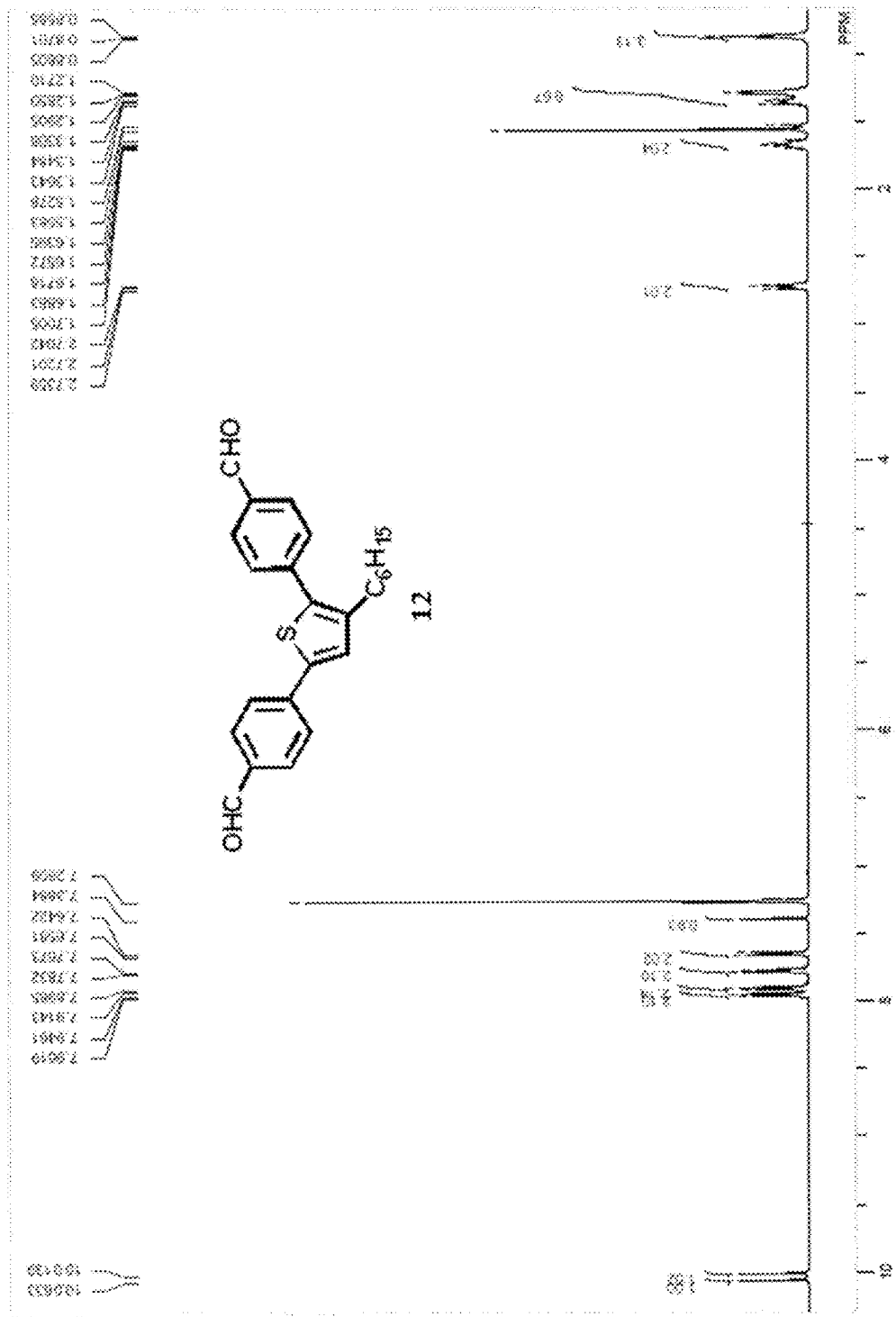
FIG. 16A is a proton nuclear magnetic resonance ($^1$H NMR) spectrum of a dialdehyde of Formula (VI), wherein each $R_1$ and $R_2$ are hydrogen, and $R_3$ is n-hexyl (compound 12).
Figure 16B:
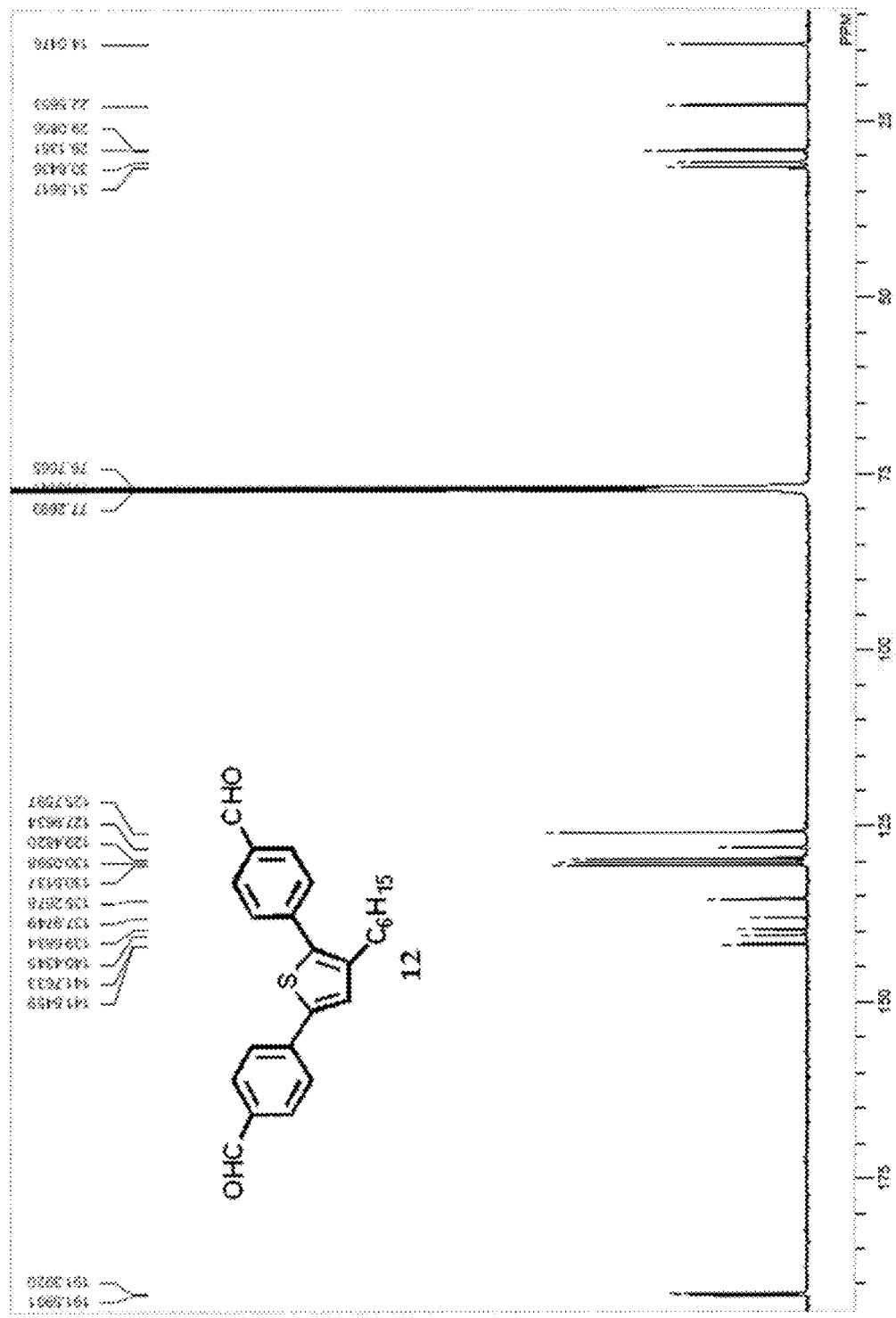
FIG. 16B is a carbon nuclear magnetic resonance ($^{13}$C NMR) spectrum of a dialdehyde of Formula (VI), wherein each $R_1$ and $R_2$ are hydrogen, and $R_3$ is n-hexyl (compound 12).

The electronic states, i.e. HOMO/LUMO levels (ionization potential/electronic affinity), of the copolymers were investigated using CV, which is widely used to estimate HOMO and LUMO energy levels of the conjugated polymers since the onset oxidation and reduction potentials obtained from the cyclic voltammograms correspond to the HOMO and LUMO energy levels, respectively. The voltammograms of P1-P4 thin films coated over a gold disc electrode were recorded in dry acetonitrile, with teterabutylammonium perchlorate (TBAPC) as the supporting electrolyte at a scan rate of 100 mV/s at room temperature (FIGS. 8A and 8B). A platinum sheet was used as an auxiliary electrode, and Ag/AgCl/3M KCl was employed as the reference electrode. All measurements were calibrated with ferrocene/ferrocenium (Fc/Fc$^+$) standard. The current arises from the transfer of electrons between the energy levels of a working electrode and molecular energy levels of polymer film. Based on the Bredas relationship, the onset of the first oxidation potential and reduction potential can be correlated to the ionization potential ($I_p$) and electron affinity ($E_a$), respectively [Leonat, L.; Sbarcea, G.; Branzoi, I. V. *U.P.B. Sci. Bull. Ser. B* 2013, 75, 111, incorporated herein by reference in its entirety].

Band gap ($E_g$) of a material can then be determined by subtracting $E_a$ from $I_p$. Bredas relationship was employed to estimate the HOMO and LUMO levels of polymers P1-P4.

$E_{HOMO} = [(E_{ox} - E_{1/2\ Fc})] + 4.4]$ eV and $E_{LUMO} = [(E_{red} - E_{1/2\ Fc})] + 4.4]$ eV $E_g = E_{HOMO}(I_p) - E_{LUMO}(E_a)$ $E_{ox}$=onset of first oxidation potential
$E_{red}$=onset of first reduction potential
$E_{1/2\ Fc}$=half wave potential of Fc $E_{1/2\ Fc}$ was found to be 0.43 V which was used in Bredas equation to calculate energy levels of both the polymers which revealed a quasi-reversible oxidation behaviour, a characteristics of p-type doping, indicating that the bulk of the charge was carried out by the holes. Whereas the $E_{ox}$ for P1 and P2 was found to be 1.27 and 1.86 V, respectively, the $E_{red}$ turned out to be −0.92 and −0.71 V. Similarly, $E_{ox}$ for P3 and P4 was determined to be 1.14 and 1.29 V, the $E_{red}$ was −0.90 and −0.65 V, respectively. The formal potential ($E^{0'}$) value for poly(phenylene vinylene), P1 and P2, was found to be slightly higher than that of the cyanovinylenes, P3 and P4, presumably due to the presence of the cyano group in the latter case. The energy level diagram of P1-P4 is presented in FIGS. 9A-9D. The HOMO levels (ionization potentials) for P1-P4 derived from the onset oxidation potentials, were found to be 5.24, 5.83, 5.11 and 5.26 eV, respectively. Similarly, the LUMO levels of P1-P4, calculated from the onset of first reduction potential, were determined to be between 3.04-3.32. Consequently, the band gaps calculated for P1-P4 were found to be 2.19, 2.57, 2.04 and 1.97, respectively (FIG. 6). These data have been summarized in Table 3.

TABLE 3

Cyclic voltammetry data for P1-P4
Cyclic Voltammetry

| Polymers | Onset $E_{Ox}$ (V) | Onset $E_{Red}$ (V) | LUMO (eV) | HOMO (eV) | Band Gap (eV) |
|---|---|---|---|---|---|
| P1 | 1.27 | −0.92 | 3.05 | 5.24 | 2.19 eV |
| P2 | 1.86 | −0.71 | 3.26 | 5.83 | 2.57 eV |
| P3 | 1.14 | −0.90 | 3.07 | 5.11 | 2.04 eV |
| P4 | 1.29 | −0.65 | 3.32 | 5.26 | 1.94 eV |

EXAMPLE 10

Iodine Sensing Studies

The iodine sensing properties of polymers P1-P4 was studied by adding aliquots of aqueous solutions of metal halides or tetrabutylammonium halides to the polymer solution in THF. The initial colorless solution of polymer in THF changed to yellow color when the solutions of iodide salts were added. Moreover, the intensity of the yellow color increased with increasing time (Table 4). To verify the anionic specificity, assays of these polymers with other salts including NaCl, NaF, NaBr, NaCN and $NH_4NO_3$ were performed under identical conditions whereby the color of all mixture solutions stayed unchanged, i.e. colorless (FIGS. 10A-10D).

The addition of aqueous solutions of iodide salt to the polymers solution in THF produced two absorption including a high intensity absorption at around 295 nm and a relatively low intensity absorption at around 365 nm. In addition, the absorption intensity of polymers upon the addition of iodide salts was commensurable with their concentration (FIGS. 12A-D, 13A-D, 14A-D and 15A-D and Table 5). The Stern-Volmer Constant (Ksv) values were calculated from the time and concentration dependent absorption studies of each polymer (Table 6). The concentration of solution of iodide salt was diluted to 12.5-0.097 mM whereas absorbance was measured after every interval of 45 minutes (FIGS. 12A-D, 13A-D, 14A-D, and 15A-D). In general, a higher Ksv value indicates a higher sensitivity of the polymer [Martin, A.; Narayanaswamy, R. *Sens. Actuator B-Chem.* 1997, 38-39, 330, incorporated herein by reference in its entirety]. Polymers P1 and P3 have higher Ksv values and hence have shown greater sensitivity compared to P2 and P4. The LOD of each polymer calculated by IUPAC method [Shrivastava, A.; Gupta, V. B. *Chron. Young Sci.* 2011, 2, 21, incorporated herein by reference in its entirety] revealed that the LOD for P1 and P3 were 0.53 and 0.43 mM, respectively, whereas P2 and P4 have a LOD of 0.74 and 2.54 mM, respectively (Table 5).

TABLE 4

Color changes of polymers P1-P4 upon addition of Br⁻ (NaBr, TBABr), Cl⁻ (NaCl), F⁻ (NaF), I⁻ (TBAI, NaI, KI), $NO_3^-$ ($NH_4NO_3$), and CN⁻ (NaCN). Concentrations of P1-P4 and salt concentrations are 0.0287 µM and 12.5 mM, respectively.

| Salt Solutions | P1 0 mints | P1 60 mints | P1 12 hrs | P2 0 mints | P2 60 mints | P2 12 hrs | P3 0 mints | P3 60 minutes | P3 12 hrs | P4 0 mints | P4 60 minutes | P4 12 hrs |
|---|---|---|---|---|---|---|---|---|---|---|---|---|
| TBAI | + | ++ | +++ | + | ++ | +++ | + | ++ | +++ | + | ++ | +++ |
| NaI | + | ++ | +++ | + | ++ | +++ | + | ++ | +++ | + | ++ | +++ |
| KI | + | ++ | +++ | + | ++ | +++ | + | ++ | +++ | + | ++ | +++ |
| NaF | − | − | | − | − | | − | − | | − | − | |
| $NH_4NO_3$ | − | − | | − | − | | − | − | | − | − | |
| NaCl | − | − | | − | − | | − | − | | − | − | |
| NaBr | − | − | | − | − | | − | − | | − | − | |
| NaCN | − | − | | − | − | | − | − | | − | − | |
| TBABr | − | − | | − | − | | − | − | | − | − | |

Legends:
+ = Light Yellow,
++ = Yellow,
+++ = Dark Yellow

TABLE 5

Summary of absorption spectra of P1-P4 (0.0287 µM) + Iodides (12.5 mM).

| Polymers | Broad Peak λ max (Free I⁻¹) | New intensive peak in the presence of iodides ions (nm) NaI | KI | TBAI | Linear Regression Ksv (M⁻¹) in TBAI | Correlation Coefficient | Limit of Detection (LOD) (mM) |
|---|---|---|---|---|---|---|---|
| P1 | 288 | 295 | 295 | 295 | $10.620 \times 10^3$ | $R^2 = 0.9951$ | 0.53 |
| P2 | 415 | 295 | 295 | 295 | $04.083 \times 10^3$ | $R^2 = 0.9662$ | 0.74 |
| P3 | 285 | 295 | 295 | 295 | $12.417 \times 10^3$ | $R^2 = 0.9902$ | 0.43 |
| P4 | 370 | 295 | 295 | 295 | $0.7434 \times 10^3$ | $R^2 = 0.9569$ | 2.54 |

TABLE 6

Time-(in minutes) and concentration-dependent studies of P1-P4 (0.0287 μM) with TBAI (12.5-0.097 mM)

| Concentration | P1 | | | | P2 | | | | P3 | | | | P4 | | | |
|---|---|---|---|---|---|---|---|---|---|---|---|---|---|---|---|---|
| | 0 | 45 | 90 | 180 | 0 | 45 | 90 | 180 | 0 | 45 | 90 | 180 | 0 | 45 | 90 | 180 |
| 12.5 mM | + | + | + | + | + | + | + | + | + | + | + | + | + | + | + | + |
| 6.25 mM | + | + | + | + | + | + | + | + | + | + | + | + | + | + | + | + |
| 3.125 mM | + | + | + | + | + | + | + | + | + | + | + | + | + | + | + | + |
| 1.56 mM | + | + | + | + | + | + | + | + | + | + | + | + | + | + | + | + |
| 0.78 mM | + | + | + | + | + | + | + | + | + | + | + | + | + | + | + | + |
| 0.39 mM | + | + | + | + | + | + | + | + | + | + | + | + | − | − | − | − |
| 0.195 mM | − | + | + | + | − | + | + | + | − | + | + | + | − | − | − | − |
| 0.097 mM | − | + | + | + | − | − | − | − | − | + | + | + | − | − | − | − |

The invention claimed is:

1. A copolymer of Formula (I)

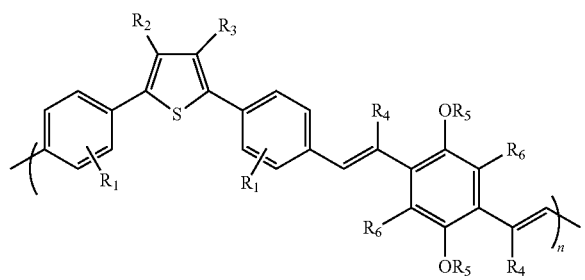

(I)

or a salt thereof, a solvate thereof, a tautomer thereof, a stereoisomer thereof, or a mixture thereof;

wherein:

each $R_1$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano;

$R_2$ and $R_3$ are independently selected from the group consisting of a hydrogen, an optionally substituted alkyl, an optionally substituted cycloalkyl, an optionally substituted arylalkyl, an optionally substituted alkoxy, an optionally substituted alkanoyl, and an optionally substituted aroyl;

each $R_4$ is a hydrogen, or a cyano;

each $R_5$ is selected from the group consisting of an optionally substituted alkyl, an optionally substituted cycloalkyl, an optionally substituted aryl, and an optionally substituted arylalkyl;

each $R_6$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano; and n is a positive integer in the range of 2-10,000.

2. The copolymer of claim 1, wherein each $R_1$ and $R_6$ are a hydrogen;

$R_2$ and $R_3$ are independently a hydrogen or an optionally substituted alkyl; and each $R_5$ is an optionally substituted alkyl.

3. The copolymer of claim 2, wherein $R_2$ and $R_3$ are independently a hydrogen or hexyl; and each $R_5$ is 2-ethylhexyl or dodecyl.

4. The copolymer of claim 1, which has a formula selected from the group consisting of

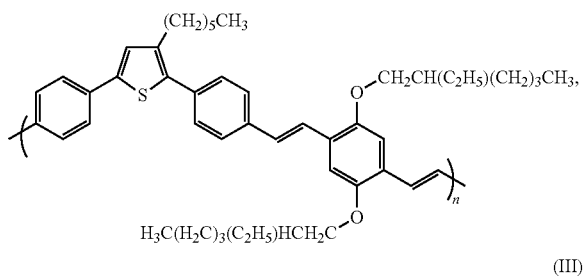

(II)

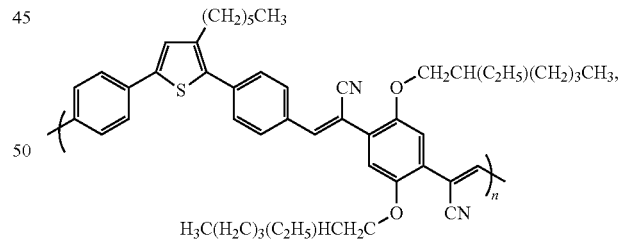

(III)

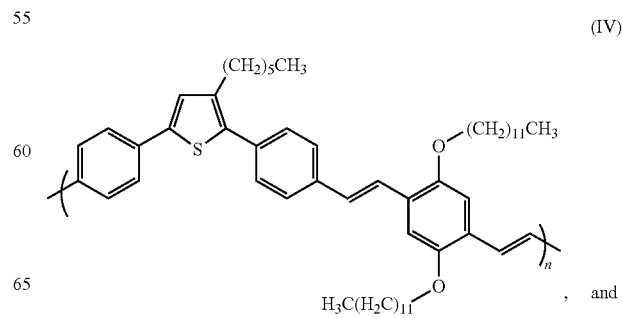

(IV)

, and

-continued

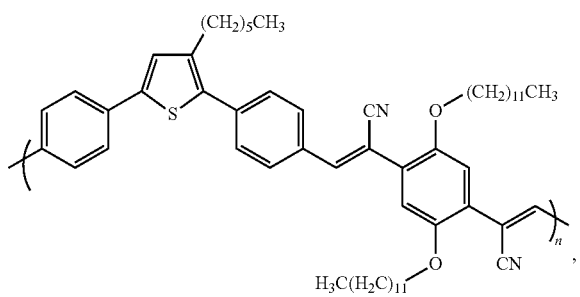

(V)

wherein n is a positive integer in the range of 2-10,000 for each of Formulae (II)-(V).

5. The copolymer of claim 1, which has an ultraviolet visible absorption with an absorption peak of 375-450 nm.

6. The copolymer of claim 1, which has a fluorescence emission peak of 520-590 nm upon excitation at a wavelength of 380-400 nm.

7. The copolymer of claim 1, which has a band gap energy of 1.8-2.7 eV.

8. A method of producing the copolymer of claim 1, wherein each $R_4$ is a hydrogen, the method comprising:
reacting a dialdehyde of Formula (VI)

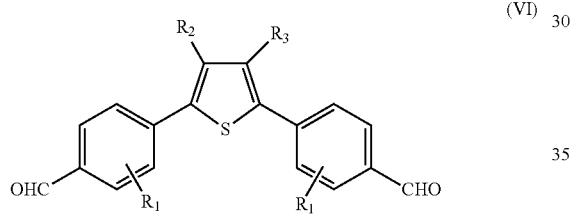

(VI)

or a salt, solvate, tautomer or stereoisomer thereof, with a diphosphonate of Formula (VII)

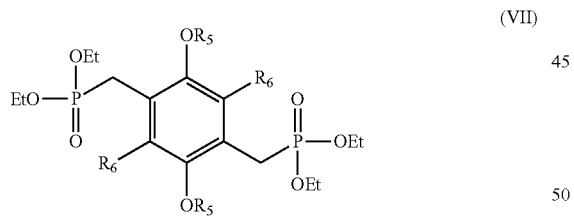

(VII)

or a salt, solvate, tautomer or stereoisomer thereof in the presence of a base to form the copolymer, wherein:
each $R_1$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano;
$R_2$ and $R_3$ are independently selected from the group consisting of a hydrogen, an optionally substituted alkyl, an optionally substituted cycloalkyl, an optionally substituted arylalkyl, an optionally substituted alkoxy, an optionally substituted alkanoyl, and an optionally substituted aroyl;
each $R_5$ is selected from the group consisting of an optionally substituted alkyl, an optionally substituted cycloalkyl, an optionally substituted aryl, and an optionally substituted arylalkyl; and
each $R_6$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano.

9. The method of claim 8, wherein a molar ratio of the dialdehyde to the diphosphonate is in the range of 1:2 to 2:1.

10. A method of producing the copolymer of claim 1, wherein each $R_4$ is a cyano, the method comprising:
reacting a dialdehyde of Formula (VI)

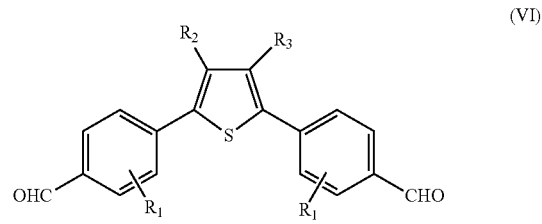

(VI)

or a salt, solvate, tautomer or stereoisomer thereof with a dinitrile of Formula (VIII)

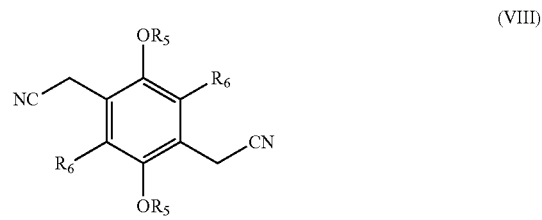

(VIII)

or a salt, solvate, tautomer or stereoisomer thereof in the presence of a base to form the copolymer, wherein:
each $R_1$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano;
$R_2$ and $R_3$ are independently selected from the group consisting of a hydrogen, an optionally substituted alkyl, an optionally substituted cycloalkyl, an optionally substituted arylalkyl, an optionally substituted alkoxy, an optionally substituted alkanoyl, and an optionally substituted aroyl;
each $R_5$ is selected from the group consisting of an optionally substituted alkyl, an optionally substituted cycloalkyl, an optionally substituted aryl, and an optionally substituted arylalkyl; and
each $R_6$ is independently selected from the group consisting of a hydrogen, an optionally substituted alkyl, an optionally substituted cycloalkyl, an optionally substituted arylalkyl, an optionally substituted aryl, an optionally substituted alkoxy, an optionally substituted alkanoyl, an optionally substituted aroyl, a halogen, a nitro, and a cyano.

11. The method of claim 10, wherein a molar ratio of the dialdehyde to the dinitrile is in the range of 1:2 to 2:1.

12. A method of detecting $I^-$ anions in a fluid sample, comprising:
    contacting the fluid sample with the copolymer of claim 1 to form a mixture; and
    measuring an ultraviolet visible absorption profile of the mixture to determine a presence of $I^-$ anions in the fluid sample;
    wherein an ultraviolet visible absorption peak at 290-300 nm and/or 360-370 nm indicates the presence of $I^-$ anions.

13. The method of claim 12, wherein the fluid sample comprises greater than 10% v/v of water as a solvent and wherein the fluid sample is at least one selected from the group consisting of contaminated water, a consumable good, and a bodily fluid.

14. The method of claim 12, wherein the copolymer is present in the mixture at a concentration of 1-1,000 nM.

15. The method of claim 12, wherein the copolymer is contacted with the fluid sample for 1 second to 24 hours.

16. The method of claim 12, which has an $I^-$ anion detection lower limit of 0.3-2.6 mM in the presence of one or more additional anions and counter cations.

17. The method of claim 16, wherein the one or more additional anions are at least one selected from the group consisting of $Br^-$, $Cl^-$, $F^-$, $NO_3^-$, and $CN^-$.

18. The method of claim 16, wherein the one or more additional counter cations are at least one selected from the group consisting of $Na^+$, $K^+$, $NH_4^+$, and $N[(CH_2)_3CH_3]_4^+$.

19. A membrane, comprising:
    a polymer selected from the group consisting of polyvinyl chloride, polystyrene, polyethylene, and poly(methyl methacrylate); and
    0.1 to 75 wt % of the copolymer of claim 1 relative to a total weight of the membrane, wherein the copolymer is dispersed with the polymer.

20. The membrane of claim 19, which is further supported by a substrate.

\* \* \* \* \*